United States Patent
Robin

(10) Patent No.: US 10,240,918 B2
(45) Date of Patent: Mar. 26, 2019

(54) METHOD FOR STUDYING A ZONE OF AN OBJECT SO AS TO DETERMINE A MASS-THICKNESS AND A COMPOSITION THEREOF BY USING AN ELECTRON BEAM AND MEASUREMENTS OF X-RAY RADIATION INTENSITY

(71) Applicant: COMMISSARIAT A L'ENERGIE ATOMIQUE ET AUX ENERGIES ALTERNATIVES, Paris (FR)

(72) Inventor: Eric Robin, Manthes (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 152 days.

(21) Appl. No.: 14/966,932

(22) Filed: Dec. 11, 2015

(65) Prior Publication Data

US 2016/0169668 A1 Jun. 16, 2016

(30) Foreign Application Priority Data

Dec. 12, 2014 (FR) .................... 14 62333

(51) Int. Cl.
*G01B 15/02* (2006.01)
*G01N 23/2252* (2018.01)
(Continued)

(52) U.S. Cl.
CPC ......... *G01B 15/02* (2013.01); *G01N 23/2252* (2013.01); *H01J 37/244* (2013.01);
(Continued)

(58) Field of Classification Search
CPC ............................ G01B 15/02; G01N 23/2252
(Continued)

(56) References Cited

U.S. PATENT DOCUMENTS 3,753,619 A * 8/1973 Thorpe .................. G01J 3/453
356/451
6,654,125 B2 * 11/2003 Maynard ................ G01J 3/453
356/451

(Continued)

OTHER PUBLICATIONS

Watanabe et al., "The quantitative analysis of thin specimens: a review of progress from the Cliff-Lorimer to the new x-factor methods", Journal of Microscopy, vol. 221, No. 2, Feb. 2006, pp. 89-109; cited in the FSR (in English).

(Continued)

*Primary Examiner* — Ricky Ngon
(74) *Attorney, Agent, or Firm* — Westerman, Hattori, Daniels & Adrian, LLP

(57) ABSTRACT

A method for studying a zone of an object, the zone exhibiting a mass-thickness and comprising at least one chemical element, the method including a step of exposing a part of the zone of the object to an electron beam, a step of identifying each chemical element present in the said zone by virtue of the exposure step, a step of measuring, for each chemical element identified, a corresponding intensity of an X-ray radiation emergent from the object on account of the said exposure step, a step of determining a value of the said mass-thickness dependent on each measurement step, and a step of determining a value of the concentration of each chemical element identified using the said value of the mass-thickness determined.

21 Claims, 4 Drawing Sheets

Figure 1:
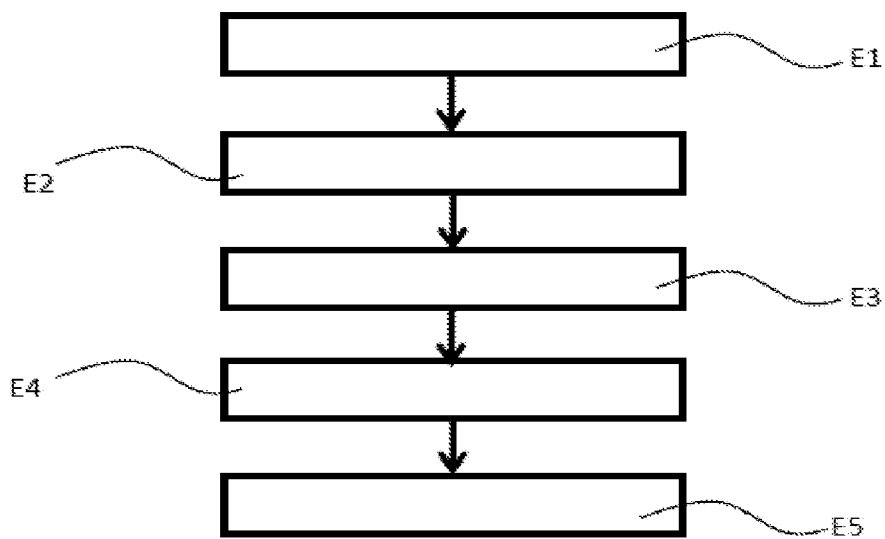

(51) Int. Cl.
*H01J 37/244* (2006.01)
*H01J 37/285* (2006.01)

(52) U.S. Cl.
CPC ........ *H01J 37/285* (2013.01); *G01N 2223/61* (2013.01); *G01N 2223/633* (2013.01); *G01N 2223/66* (2013.01)

(58) Field of Classification Search
USPC .......................................................... 702/172
See application file for complete search history.

(56) References Cited

U.S. PATENT DOCUMENTS

| | | | | |
|---|---|---|---|---|
| 2004/0125913 | A1* | 7/2004 | Larson | G01B 15/02 378/50 |
| 2006/0291619 | A1* | 12/2006 | Statham | G01N 23/22 378/45 |
| 2008/0249380 | A1* | 10/2008 | Van Beek | A61B 5/0059 600/310 |
| 2011/0243301 | A1* | 10/2011 | Watanabe | G01N 23/223 378/46 |

OTHER PUBLICATIONS

Gauvin, "What Remains to Be Done to Aloow Quantitative X-Ray Microanalysis Performed with EDS to Become a True Characterization Technique?" Microscopy and Microanalysis, vol. 18, Oct. 2012, pp. 915-940; cited in the FSR (in English).

Horny et al., "Development of a New Quantitative X-Ray Microanalysis Method for Electron Microscopy", Microscopy and Microanalysis, vol. 16, Dec. 2010, pp. 821-830; cited in the FSR (in English).

French Search Report dated Jun. 25, 2015 issued in counterpart French Application No. 14 62333; with English partial translation and partial machine translation (11 pages).

* cited by examiner

METHOD FOR STUDYING A ZONE OF AN OBJECT SO AS TO DETERMINE A MASS-THICKNESS AND A COMPOSITION THEREOF BY USING AN ELECTRON BEAM AND MEASUREMENTS OF X-RAY RADIATION INTENSITY

TECHNICAL FIELD OF THE INVENTION

The invention relates to the field of object study, for example by energy dispersive or wavelength dispersive spectrometry in an electron microscope, of which it is sought to characterize a zone by determining its mass-thickness and its composition in terms of chemical element(s).

The subject of the invention is more particularly a method for studying a zone of the object, the said zone exhibiting a mass-thickness and comprising at least one chemical element. The method of study accordingly uses in particular an electron beam and X-ray radiation intensity measurements deriving from the interaction of the beam with the said zone.

PRIOR ART

To determine the composition of a wafer made of a material, in particular homogeneous, it is known to use measurements based on energy dispersive or wavelength dispersive spectrometry using, for example, scanning electron microscopes (SEM) or transmission electron microscopes (TEM).

A first known scheme is limited to studying an object, for example taking the form of a wafer as mentioned hereinabove, whose thickness is such that the electron beam interacting with the said object is entirely absorbed by the said object. It is then assumed that the thickness of the wafer is infinite.

A second known scheme is limited to studying an object, for example taking the form of a wafer as mentioned hereinabove, which is totally transparent to the electron beam used during the study. It is then assumed that the thickness of the wafer is zero.

These two schemes give approximate but unsatisfactory results. In particular, these results are erroneous when the thickness of the object is such that part of the electron beam is transmitted by the said object.

OBJECT OF THE INVENTION

The aim of the present invention is to propose a solution making it possible to take into account the thickness of the object over the zone studied.

This aim is addressed by virtue of a method for studying a zone of an object, the said zone exhibiting a mass-thickness and comprising at least one chemical element, the said method comprising:
- a step of exposing a part of the zone of the object to an electron beam,
- a step of identifying each chemical element present in the said zone by virtue of the exposure step,
- a step of measuring, for each chemical element identified, a corresponding intensity of an X-ray radiation emergent from the object on account of the said exposure step,
- a step of determining a value of the said mass-thickness dependent on each measurement step,
- a step of determining a value of the concentration of each chemical element identified using the said value of the mass-thickness determined.

The method also comprises an initialization step in which an intermediate value of the mass-thickness $\rho z_0$, with $\rho$ the assumed density and $z_0$ the assumed thickness of the object at the level of the said zone, and an intermediate value of concentration $C_{ic}$ of each chemical element identified are determined by choice, especially by considering that the intensity of the corresponding emergent X-ray radiation is equal to the intensity of the radiation generated in the object by the said corresponding chemical element, and the method comprises an iterative cycle of steps comprising for each iteration of the said cycle:
- a step of calculating an incidence correction term $\overline{\Theta}$ intended to take account of the angle of incidence $\theta$ of the electron beam and associated with the zone studied,
- a fitting step, implemented for each chemical element identified, and comprising:
    - a step of calculating an incidence correction term $\overline{\Theta}_{im}$ associated with the said chemical element identified and intended to take account of the angle of incidence $\theta$ of the electron beam,
    - a step of calculating an atomic number correction term $\overline{\varphi}_i$ for the said corresponding chemical element using the incidence correction terms $\overline{\Theta}$ and $\overline{\Theta}_{im}$ calculated in the course of the said cycle,
    - a step of calculating an absorption correction term $\overline{\chi}_i$ for the said corresponding chemical element using the incidence correction terms $\overline{\Theta}$ and $\overline{\Theta}_{im}$ calculated in the course of the said cycle, and the atomic number correction term $\overline{\varphi}_i$ calculated in the course of the said cycle,
- a step of modifying the intermediate value of mass-thickness $\rho z_0$ using the incidence correction term $\overline{\Theta}$ calculated in the course of the said cycle, and the incidence correction $\overline{\Theta}_{im}$, atomic number correction $\overline{\varphi}_i$ and absorption correction $\overline{\chi}_i$ terms calculated in the course of the said cycle for each chemical element and dependent on each measurement step,
- a step of modifying, for each chemical element, the intermediate value of concentration $C_{ic}$ of the said corresponding chemical element using the intermediate value of mass-thickness $\rho z_0$ as modified in the course of the said cycle, the incidence correction term $\overline{\Theta}$ calculated in the course of the said cycle and the incidence correction $\overline{\Theta}_{im}$, atomic number correction $\overline{\varphi}_i$ and absorption correction $\overline{\chi}_i$ terms calculated in the course of the said cycle and corresponding to the said chemical element, and the iteration is halted when the variation, between two successive iterations of the intermediate values of mass-thickness $\rho z_0$ and of the intermediate values of concentration $C_{ic}$ of each chemical element, is less than an associated predetermined threshold, the said modified intermediate mass-thickness value defining the mass-thickness value determined and each modified intermediate concentration value defining the corresponding concentration value determined.

According to one embodiment, each step of calculating the incidence correction term $\overline{\Theta}$ comprises the solving of the following equation:

$$\overline{\Theta} = \left\{ 1 + \left[ \frac{\rho z_0}{\cos\theta} f(\mathcal{Z}_c) - 2\frac{\cos\theta}{\rho}\left(1 - e^{14(1-\rho)\frac{\rho z_0}{\cos\theta}f(\mathcal{Z}_c)}\right)e^{-2\frac{\rho z_0}{\cos\theta}f(\mathcal{Z}_c)} \right]\left[\frac{1}{\cos\theta} - 1\right] \right\}^{0.6}$$

and each step of calculating the incidence correction term $\overline{\Theta}_{im}$ comprises the solving of the following equation:

$$\overline{\Theta}_{im} = \left\{ 1 + \left[ \frac{\rho z_{im}}{\cos\theta} f_m(E_{is}) - 2\frac{\cos\theta}{\rho} e^{-2\frac{\rho z_{im}}{\cos\theta} f_m(E_{is})} \right] \left[ \frac{1}{\cos\theta} - 1 \right] \right\}^{0.6}$$

with $Z_c$ the mean atomic number of the object at the level of the said zone, $f(Z_c)$ a function of the mean atomic number $Z_c$, $z_{im}$ the maximum ionization depth of the corresponding chemical element, $f_m(E_{is})$ a function of the ionization threshold energy $E_{is}$ of the energy level considered of a corresponding chemical element.

For example, we have $$f(Z_c) = e^{a(LnZ_c)^4 + b(LnZ_c)^3 + c(LnZ_c)^2 + dLnZ_c + e},$$

with a, b, c, d, e parameters determined by Monte-Carlo simulation and depending on the energy of the electrons of the said electron beam.

In particular, $$f_m(E_{is}) = \frac{A E_{is}^m}{(R_p/S_p)_i}$$

with $(R_p/S_p)_i$ being the ratio of the backscattering coefficients $R_p$ and of the stopping power $S_p$ for the corresponding pure chemical element, and A and m parameters determined by Monte-Carlo simulation and depending on the energy level for the said corresponding chemical element.

According to one embodiment, each step of calculating the atomic number correction term $\overline{\varphi}_i$ uses the following relation $$\overline{\varphi}_i(\rho z_\theta) = \frac{1 + \alpha(\rho z_\theta)^n}{1 + \frac{\alpha C_{ic}}{\xi_i I_{igco}} \frac{(\rho z_\theta)^{(1+n)}}{\left(1 + \frac{\beta_i}{(\rho z_\theta)^n}\right)}}$$

with $I_{igco}$ the intensity per unit time of an X-ray radiation generated by the corresponding chemical element in the object considered to be opaque to the said electron beam, $\xi_i$ the zeta-factor associated with the said corresponding chemical element, n a parameter depending on the mean atomic number Zc of the object at the level of the said zone, $\alpha$ a parameter depending on the mean atomic number Zc of the object at the level of the said zone, $\beta_i$ a term making it possible to fit the maximum of the term $\overline{\varphi}_i$ and $z_\theta$ the thickness in the direction of incidence $\theta$ determined on the basis of the incidence correction terms $\overline{\Theta}$ and $\overline{\Theta}_{im}$ calculated in the course of the said cycle.

For example, the parameter n is determined by the following relation $n = n_1 \operatorname{Ln} Z_c + n_2$, the parameters $n_1$ and $n_2$ being given by a chart giving the value of n as a function of $Z_c$ whatever the power of the electron beam.

For example, the parameter $\alpha$ is determined by the following relation $$\alpha = e^{(a_1(LnZ_c)^2 + a_2 LnZ_c + a_3)}$$

with $\alpha_1$, $\alpha_2$ and $\alpha_3$ parameters depending on the initial energy $E_0$ of the electrons of the electron beam.

According to one embodiment, the term $\beta_i$ is determined by supposing that, for any thickness greater than or equal to a maximum ionization depth $z_{im}$ of the corresponding chemical element, the intensity of the X-ray radiation generated in the object is equivalent to that of the object if the latter is opaque to the said electron beam.

In particular, according to the said embodiment, the term $\beta_i$ is obtained by solving the following equation:

$$\beta_i = \begin{cases} (\rho z_{im})^n \dfrac{\left(\dfrac{\xi_i}{C_{ic}} \dfrac{I_{gco}}{\rho z_{im}} - 1\right)}{\alpha(\rho z_{im})^n - \left(\dfrac{\xi_i}{C_{ic}} \dfrac{I_{gco}}{\rho z_{im}} - 1\right)}, & \text{if } \beta_i > 0 \\ 0, & \text{if } \beta_i \le 0 \end{cases},$$

with $z_{im}$ the maximum ionization depth of the corresponding chemical element.

According to an implementation, each step of calculating the absorption correction term $\overline{\chi}_i$ makes use of solving the equation $$\overline{\chi}_i = \begin{cases} \dfrac{\chi_{ic}\rho z_0 \varphi_i(\rho z_\theta)}{\varphi_i(0) + \dfrac{P_i}{\chi_{ic}} + \left\{P'_i\left(\dfrac{1}{\chi_{ic}} - \rho z_0\right) - \right.} \\ \quad \left. \left[\varphi_i(0) - \varphi_i(\rho z_0) + \dfrac{P_i}{\chi_{ic}}\right] + (P'_i - P_i)\rho z_{ib}\right\} \\ \quad e^{-\chi_{ic}\rho z_{ib}} - \left[\varphi_i(\rho z_0) + \dfrac{P_i}{\chi_{ic}}\right]e^{-\chi_{ic}\rho z_0}, & \text{if } z_{ib} > 0 \\ \dfrac{\rho z_0 \chi_{ic}\varphi_i(\rho z_\theta)}{\varphi_i(0) + \dfrac{P''_i}{\chi_{ic}} - \left\{P''_i\left(\dfrac{1}{\chi_{ic}} + \rho z_0\right) + \varphi_i(0)\right\}e^{-\chi_{ic}\rho z_0}}, & \text{if } z_{ib} \le 0 \end{cases}$$

with $\varphi_i(0)$ the value of the distribution of the intensities of the X-ray radiation generated at the surface of the object by the corresponding chemical element, $\varphi_i(\rho z_0)$ the value of the distribution of the intensities of the X-ray radiation generated at the depth $z_0$ of the object by the corresponding chemical element, $P_i$ the initial slope of the distribution of the intensities of the X-ray radiation generated at the surface of the object by the corresponding chemical element and determined by the relation $$P_i = \frac{g \cdot h^4 \cdot (F/\overline{R})^2}{\overline{\varphi}_i(\rho z_{i\theta})\rho z_{i\theta}} \frac{1}{(\cos\theta)^4} \text{ with}$$

$$\overline{\varphi}_i(\rho z_{i\theta}) = \frac{1 + \alpha(\rho z_\theta)^n}{1 + \frac{\alpha C_{ic}}{\xi_i I_{igco}} \frac{(\rho z_\theta)^{(1+n)}}{\left(1 + \frac{\beta_i}{(\rho z_\theta)^n}\right)}} \text{ and } z_{i\theta} = \frac{z_{im}}{\overline{\Theta}_{im}\cos\theta},$$

$\chi_{ic}$ representing the mass absorption coefficient of the compound for the characteristic X-ray radiation of the corresponding chemical element, $\overline{\varphi}_i(\rho z_\theta)$ being the atomic number correction term calculated in the course of the said cycle, $$P'_i = \frac{[\varphi_i(0) - \varphi_i(\rho z_0)]^2 + 2P_i\rho z_0[\overline{\varphi}_i(\rho z_\theta) - \varphi_i(\rho z_0)]}{\rho z_0[2\overline{\varphi}_i(\rho z_\theta) - 2\varphi_i(0) - P_i\rho z_0]},$$

-continued $$P_i'' = 2\frac{\overline{\varphi}_i(\rho z_0) - \varphi_i(0)}{\rho z_0},$$

$$z_{ib} = z_0 \frac{2\overline{\varphi}_i(\rho z_0) - \varphi_i(0) - \varphi_i(\rho z_0)}{P_i \rho z_0 + \varphi_i(0) - \varphi_i(\rho z_0)},$$

$z_{im}$ the maximum ionization depth of the corresponding chemical element, $\beta_i$ a term making it possible to fit the maximum of the atomic number correction term, $I_{igco}$ the intensity per unit time of an X-ray radiation generated by the corresponding chemical element in the object considered to be opaque to the said electron beam, $\xi_i$ the zeta-factor associated with the said corresponding chemical element, $\alpha$ a parameter depending on the mean atomic number Zc of the object at the level of the said zone, n a parameter depending on the mean atomic number Zc of the object at the level of the said zone and $z_\theta$ the depth of the object at the level of the said zone while taking account of the incidence $\theta$ of the electron beam.

In particular, the parameter $\varphi_i(0)$ can be calculated in the following manner:

$$\varphi_i(0) = \begin{cases} 1 + [\varphi_{im}(0) - 1]\frac{z_0}{\overline{z}_i}, & \text{if } z_0 < \overline{z}_i \\ \varphi_{im}(0), & \text{if } z_0 \geq \overline{z}_i \end{cases} \text{ with}$$

$$\overline{z}_i = z_{ip}\frac{\rho_i}{\rho}\frac{n}{n_i}\left[1 + 0.048\left(2.5 - \frac{E_0}{20}\right)\left(1 - LnM_i + \frac{(LnM_i)^2}{3}\right)\left(\frac{M_c}{M_i} - 1\right)\right],$$

$\varphi_i(0)$ the surface ionization of the corresponding chemical element in the object considered to be opaque to the said electron beam, $\overline{z}_{ip}$ the thickness for which the atomic number correction term $\overline{\varphi}_i$ for the corresponding pure chemical element is a maximum, n and $n_i$ parameters depending respectively on the mean atomic number of the object and on the atomic number of the pure chemical element, $\rho_i$ the density of the corresponding pure chemical element and $M_c$ and $M_i$ the atomic masses of the object and of the corresponding pure chemical element, and $E_0$ the initial energy of the electrons of the electron beam.

The method can comprise a step of determining a parameter $\overline{z}_{i\theta}$ corresponding to the minimum value between $\overline{z}_i$ and $z_{i\theta}$ and defined by the following relation: $\overline{z}_{i\theta}=\text{Min}(\overline{z}_i, z_{i\theta})$.

In particular, the term $\varphi_i(\rho z_0)$ is determined in the following manner:

$$\varphi_i(\rho z_0) = \begin{cases} \left\{\left[\frac{3}{2} - \varphi_i(0)\right]\frac{z_0}{\overline{z}_{i\theta}}\left[2 - \frac{z_0}{\overline{z}_{i\theta}}\right] + \varphi_i(0)\right\}\cos\theta, & \text{if } z_0 < \overline{z}_{i\theta} \\ \frac{3}{2}\left\{\left[\frac{z_0 - \overline{z}_{i\theta}}{z_{im} - \overline{z}_{i\theta}}\right]\left[\frac{z_0 - \overline{z}_{i\theta}}{z_{im} - \overline{z}_{i\theta}} - 2\right] + 1\right\} + \cos\theta, & \text{if } \overline{z}_{i\theta} \leq z_0 \leq z_{im} \\ 0 & \text{if } z_0 > z_{im} \end{cases}$$

According to a variant, the angle of incidence $\theta$ being zero then the two incidence correction terms $\overline{\Theta}$ and $\overline{\Theta}_{im}$ are equal to 1 so that the atomic number correction term is determined on the basis of the following equation $$\overline{\varphi}_i(\rho z_0) = \frac{1 + \alpha(\rho z_0)^n}{1 + \frac{\alpha C_{ic}}{\xi_i I_{igco}}\frac{(\rho z_0)^{(1+n)}}{\left(1 + \frac{\beta_i}{(\rho z_0)^n}\right)}}$$

with $I_{igco}$ the intensity per unit time of an X-ray radiation generated by the corresponding chemical element in the object considered to be opaque to the said electron beam, $\xi_i$ the zeta-factor associated with the said corresponding chemical element, n a parameter depending on the mean atomic number Zc of the object at the level of the said zone, $\alpha$ a parameter depending on the mean atomic number Zc of the object at the level of the said zone, $\beta_i$ a term making it possible to fit the maximum of the term $\overline{\varphi}_i$, and in that $$\overline{\chi}_i = \begin{cases} \dfrac{\chi_{ic}\rho z_0\overline{\varphi}_i(\rho z_0)}{\varphi_i(0) + \dfrac{P_i}{\chi_{ic}} + \left\{P_i'\left(\dfrac{1}{\chi_{ic}} - \rho z_0\right) - \right.} \\ \quad \left[\varphi_i(0) - \varphi_i(\rho z_0) + \dfrac{P_i}{\chi_{ic}}\right] + (P_i' - P_i)\rho z_{ib}\right\} \\ \quad e^{-\chi_{ic}\rho z_{ib}} - \left[\varphi_i(\rho z_0) + \dfrac{P_i}{\chi_{ic}}\right]e^{-\chi_{ic}\rho z_0}, & \text{if } z_{ib} > 0 \\[2mm] \dfrac{\rho z_0 \chi_{ic}\overline{\varphi}_i(\rho z_0)}{\varphi_i(0) + \dfrac{P_i''}{\chi_{ic}} - \left\{P_i''\left(\dfrac{1}{\chi_{ic}} + \rho z_0\right) + \varphi_i(0)\right\}e^{-\chi_{ic}\rho z_0}}, & \text{if } z_{ib} \leq 0 \end{cases}$$

with $$\varphi_i(\rho z_0) = \begin{cases} \left[\frac{3}{2} - \varphi_i(0)\right]\frac{z_0}{\overline{z}_i}\left[2 - \frac{z_0}{\overline{z}_i}\right] + \varphi_i(0), & \text{if } z_0 < \overline{z}_i \\ \frac{3}{2}\left\{\left[\frac{z_0 - \overline{z}_i}{z_{im} - \overline{z}_i}\right]\left[\frac{z_0 - \overline{z}_i}{z_{im} - \overline{z}_i} - 2\right] + 1\right\}, & \text{if } \overline{z}_i \leq z_0 \leq z_{im} \\ 0 & \text{if } z_0 > z_{im} \end{cases}$$

$\varphi_i(0)$ the value of the distribution of the intensities of the X-ray radiation generated at the surface of the object by the corresponding chemical element, $P_i$ the initial slope of the distribution of the intensities of the X-ray radiation generated at the surface of the object by the corresponding chemical element and determined by the relation $$P_i = \frac{g \cdot h^4 \cdot (F/R)^2}{\overline{\varphi}_i(\rho z_{im})\rho z_{im}} \text{ with } \overline{\varphi}_i(\rho z_{im}) = \frac{1 + \alpha(\rho z_{im})^n}{1 + \frac{\alpha C_{ic}}{\xi_i I_{igco}}\frac{(\rho z_{im})^{(1+n)}}{\left(1 + \frac{\beta_i}{(\rho z_{im})^n}\right)}},$$

$\chi_{ic}$ representing the mass absorption coefficient of the object for the corresponding chemical element $$P_i' = \frac{[\varphi_i(0) - \varphi_i(\rho z_0)]^2 + 2P_i\rho z_0[\overline{\varphi}_i(\rho z_0) - \varphi_i(\rho z_0)]}{\rho z_0[2\overline{\varphi}_i(\rho z_0) - 2\varphi_i(0) - P_i\rho z_0]},$$

$$P_i'' = 2\frac{\overline{\varphi}_i(\rho z_0) - \varphi_i(0)}{\rho z_0}, \text{ and}$$

$$z_{ib} = z_0\frac{2\overline{\varphi}_i(\rho z_0) - \varphi_i(0) - \varphi_i(\rho z_0)}{P_i\rho z_0 + \varphi_i(0) - \varphi_i(\rho z_0)},$$

$z_{im}$ the maximum ionization depth of the corresponding chemical element, $$\overline{z}_i = z_{ip}\frac{\rho_i}{\rho}\frac{n}{n_i}\left[1 + 0.048\left(2.5 - \frac{E_0}{20}\right)\left(1 - LnM_i + \frac{(LnM_i)^2}{3}\right)\left(\frac{M_c}{M_i} - 1\right)\right],$$

$\overline{z}_{ip}$ the thickness for which the atomic number correction term $\overline{\varphi}_i$ for the corresponding pure chemical element is a maximum, n and $n_i$ parameters depending respectively on the mean atomic number of the object and on the atomic number of the corresponding pure element, $\rho_i$ the density of the corresponding pure chemical element and $M_c$ and $M_i$ the atomic masses of the object and of the corresponding pure chemical element, $E_0$ the initial energy of the electrons of the electron beam, $\beta_i$ a term making it possible to fit the maximum of the atomic number correction term, $I_{igco}$ the intensity per unit time of an X-ray radiation generated by the corresponding chemical element in the object considered to be opaque to the said electron beam, $\xi_i$ the zeta-factor associated with the said corresponding chemical element, $\alpha$ a parameter depending on the mean atomic number Zc of the object at the level of the said zone (Z1), n a parameter depending on the mean atomic number Zc of the object at the level of the said zone.

Preferentially, in the course of each cycle the intermediate value of the mass-thickness is modified according to the following formula $$\rho z_0 = \overline{\Theta} \cos\theta \sum_{i=1}^{N} \xi_i \frac{\overline{\chi}_i I_{iec}}{\overline{\varphi}_i}$$

with N the total number of chemical elements identified, i the index of the current chemical element studied, $I_{iec}$ the intensity of the emergent X-ray radiation corresponding to the said chemical element of index i, $\overline{\chi}_i$ the absorption correction term calculated in the course of the said cycle and corresponding to the said chemical element of index i, $\xi_i$ the zeta-factor associated with the said chemical element of index i, the atomic number correction term $\overline{\varphi}_i$ calculated in the course of the said cycle and corresponding to the said chemical element of index i, $\overline{\Theta}$ the incidence correction term calculated in the course of the said cycle.

Preferentially, in the course of each cycle the intermediate value of concentration $C_{ic}$ of each chemical element is calculated according to the following formula:

$$C_{ic} = \frac{\xi_i}{\rho z_0} \frac{\overline{\chi}_i I_{iec}}{\overline{\varphi}_i} \overline{\Theta} \cos\theta$$

with $I_{iec}$ the measured intensity of the emergent X-ray radiation of the said corresponding chemical element, $\rho z_0$ the intermediate mass-thickness value modified in the course of the said cycle, $\overline{\chi}_i$ the absorption correction term for the said corresponding chemical element calculated in the course of the said cycle, $\xi_i$ the zeta-factor associated with the said corresponding chemical element, the atomic number correction term $\overline{\varphi}_i$ calculated in the course of the said cycle for the said corresponding chemical element, $\overline{\Theta}$ the incidence correction term calculated in the course of the said cycle.

The invention also relates to a method for studying an object comprising the following steps:
Dividing the object into several zones to be studied,
Implementing, for each zone, the hereinabove described method for studying the zone, with a view to determining the corresponding mass-thickness value and, for each element of the said zone, the corresponding concentration value.

SUMMARY DESCRIPTION OF THE DRAWINGS

Figure 2:
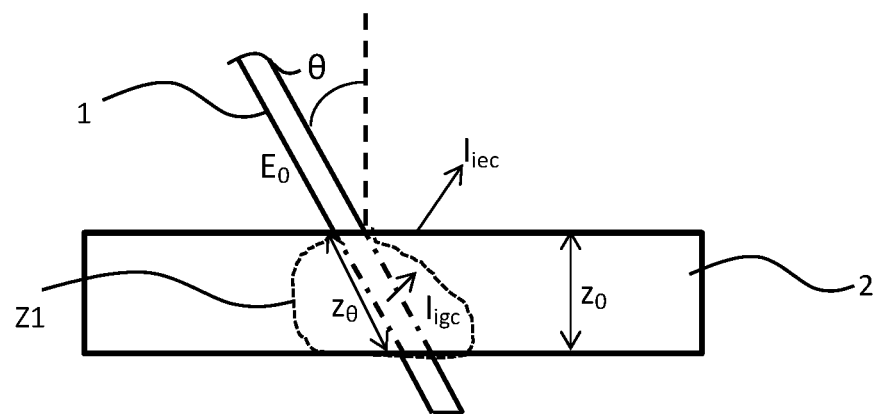
Figure 3:
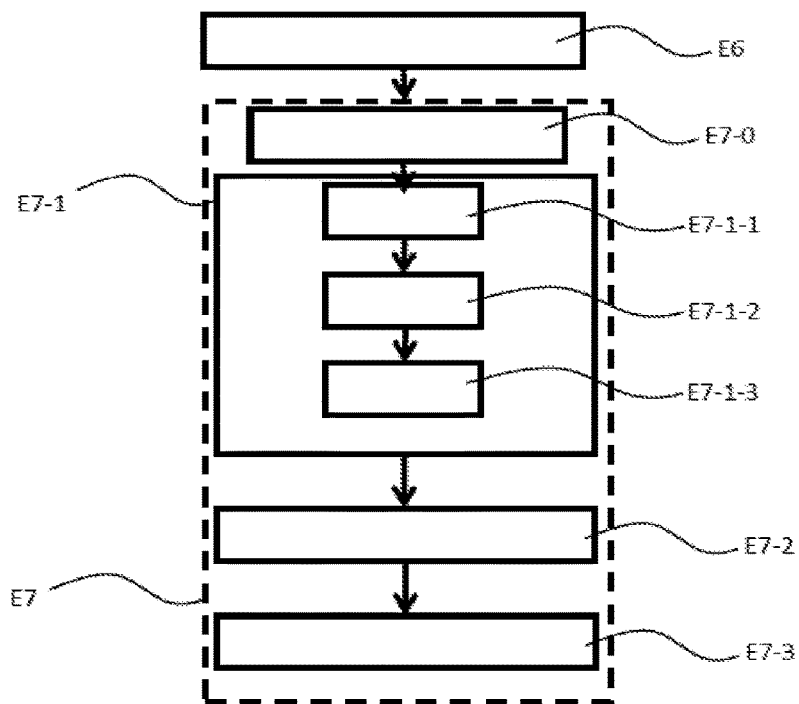
Figure 4:
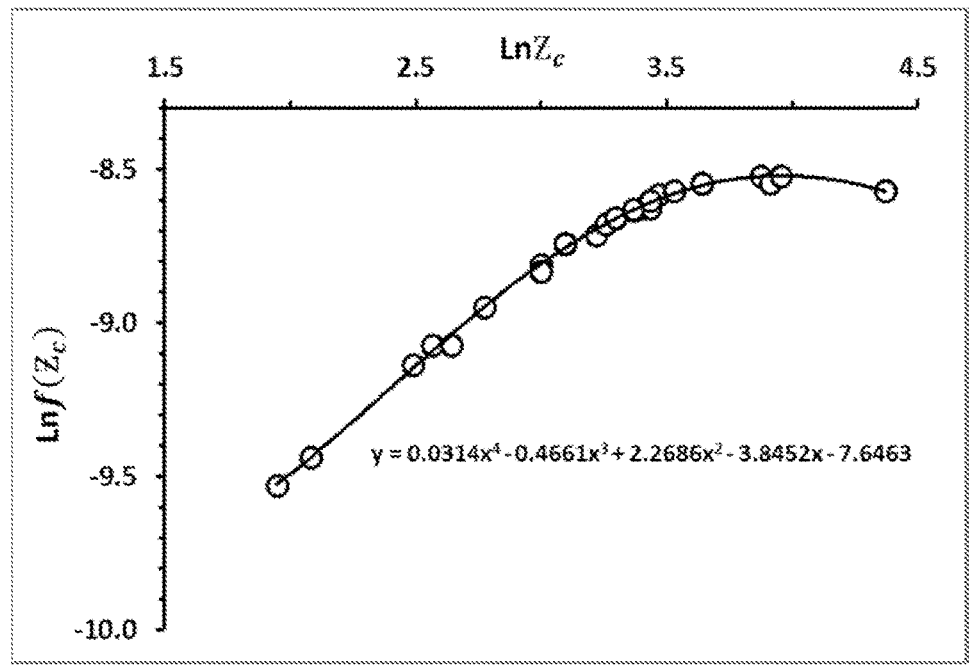
Figure 5:
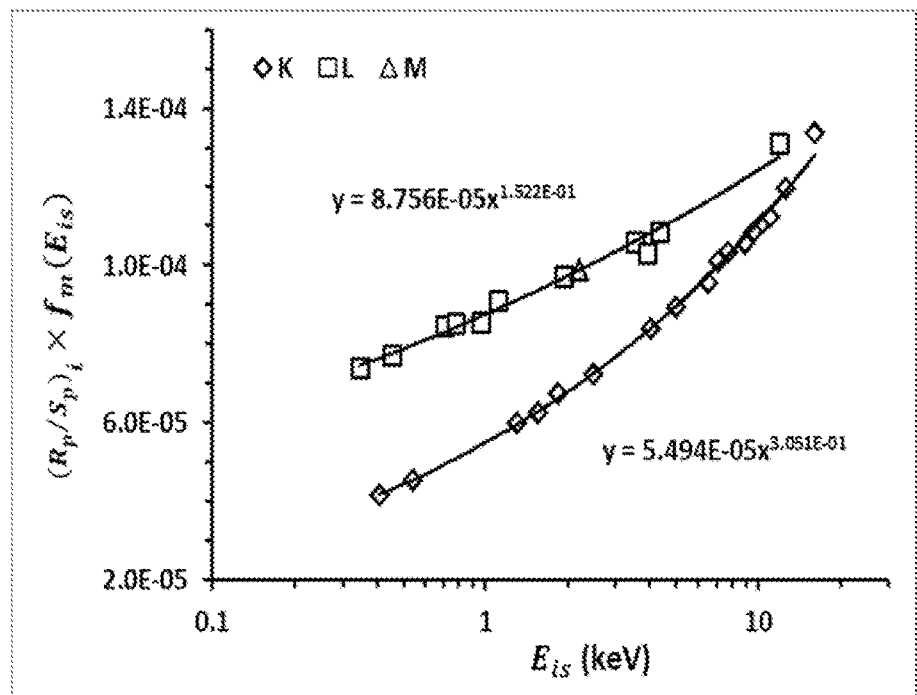
Figure 6:
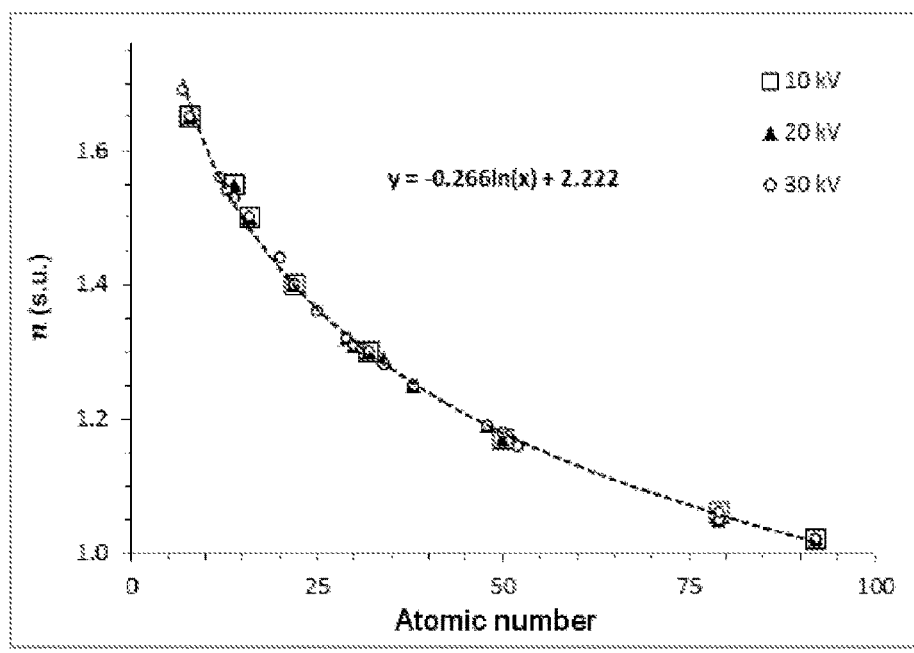
Figure 7:
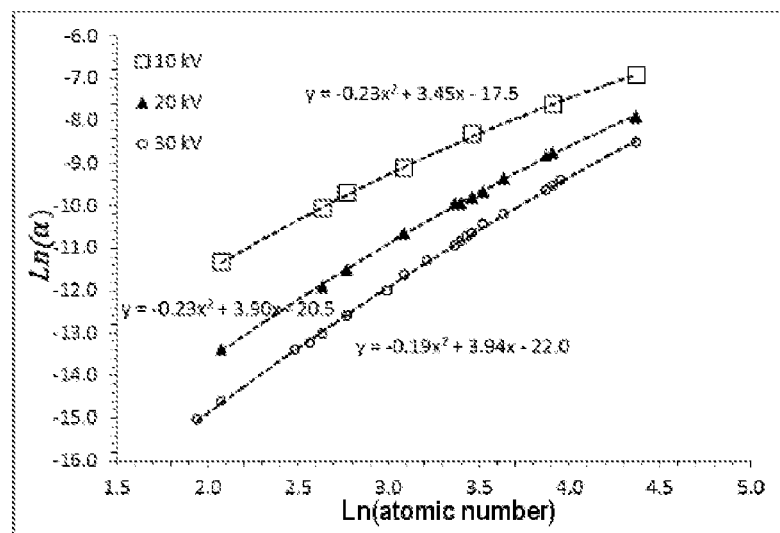
Figure 8:
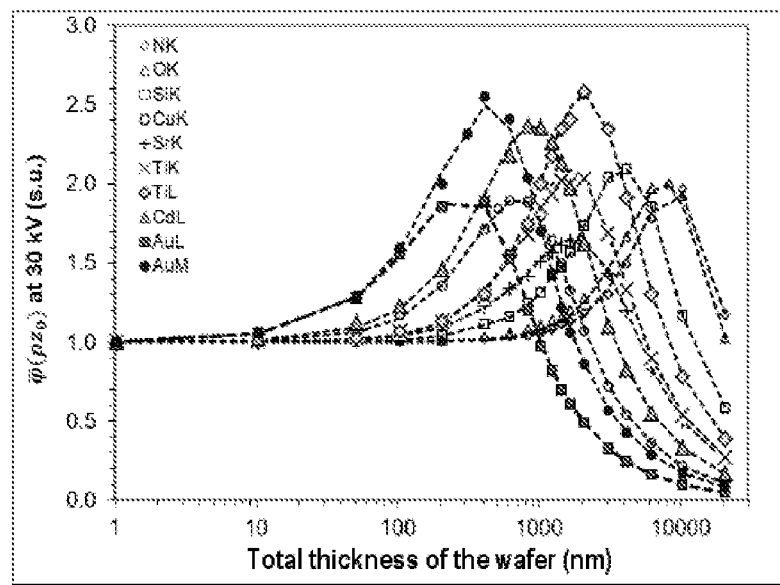

Other advantages and characteristics will emerge more clearly from the description which follows of particular embodiments of the invention which are given by way of nonlimiting examples and represented in the appended drawings, in which:

FIG. 1 schematically illustrates various steps of a method of study according to a mode of execution of the invention, FIG. 2 is a schematic view of the interaction of an electron beam with an object, FIG. 3 illustrates various steps of the method of study, FIG. 4 illustrates a way of determining parameters of a function $f(Z_c)$ by Monte-Carlo simulation, FIG. 5 illustrates a way of determining parameters of a function $f_m(E_{is})$ by Monte-Carlo simulation, the said parameters depending on the emission level K, L or M, FIG. 6 illustrates the variation of the parameter n as a function of the mean atomic number Zc for various powers of the electron beam, FIG. 7 illustrates the variation of the parameter $\alpha$ as a function of the mean atomic number Zc for various powers of the electron beam, FIG. 8 is a simulation of the atomic number correction term $\overline{\varphi}_i$ dependent on the total thickness of an object in the form of a wafer, the points are calculated by using intensities of the X-ray radiation generated by Monte-Carlo simulation and the dashed curves represent what it is possible to obtain by using the model of the method of study according to a mode of execution of the invention.

DESCRIPTION OF PREFERENTIAL MODES OF THE INVENTION

The method described hereinafter for studying a zone differs from the prior art in that the thickness of the object to be studied will be determined (that is to say not considered to be zero or infinite).

In this sense, the invention relates to a method for studying a zone of an object, the said zone exhibiting a mass-thickness and comprising at least one chemical element. The chemical element(s) will be identified in the course of the method of study. In particular, in the present description, when one speaks of a chemical element, this refers to an identified chemical element.

In the present description, "chemical element" is understood to mean an element of the periodic classification of the elements.

Generally, in the present description, when a term or a parameter comprises the index i, it is considered that this refers to a term or a parameter related to the said chemical element corresponding to this index i, i then ranging from 1 to N with N the total number of chemical elements identified.

The object can be a wafer of constant or variable thickness.

As illustrated in FIG. 1, the method of study comprises a step E1 of exposing a part of the zone of the object to an electron beam. Preferably, in contradistinction to the prior art, this exposure step is carried out in such a way that the electron beam is partially transmitted by the object.

FIG. 2 illustrates an example in which a beam 1 of electrons of energy $E_0$ interacts with the said part of the zone Z1 studied of the object 2 according to an angle of incidence $\theta$. This angle of incidence $\theta$ is given according to the normal with respect to the exterior surface of the object 2, impacted by the electron beam 1. In particular, in FIG. 2, a part of the electron beam 1 is transmitted by the object 2. The interaction of the electron beam 1 with the part of the zone Z1 results in the generation of additional X-ray radiations which will propagate in the zone studied. In particular, each chemical element i present in the zone studied will generate an X-ray radiation of intensity $I_{igc}$ which will propagate in the zone studied and part of which will be absorbed by the chemical element i of the zone and another part of which will be transmitted out of the object so as to form an emergent X-ray radiation $I_{iec}$. It is therefore understood why the zone studied is more significant than the part of the zone interacting directly with the electron beam 1.

It follows from what was stated hereinabove that when the electron beam exhibits an incidence of angle θ, this incidence is associated with a traversed thickness $z_\theta$ of the object which is in fact the thickness of the object along an axis according to which the electron beam extends. The angle θ is given between the axis of the electron beam and the normal at the level of the point of impact of the electron beam on the object. This thickness $z_\theta$ is greater than the real thickness of the object $z_0$ which is itself given according to the normal of the exterior surface of the object. This thickness $z_\theta$ can further be defined as the depth of the object at the level of the said zone studied while taking account of the incidence θ of the electron beam.

The method of study furthermore comprises a step E2 of identifying each chemical element present in the said zone Z1 by virtue of the exposure step E1. In fact, by using spectrometry techniques giving a number of ticks per second as a function of the energy, it is possible to ascertain which chemical elements are present in the zone Z1 concerned of the object 2. The general composition is then known at the level of the zone Z1 but without knowing the corresponding percentages. This may, for example, be implemented by energy dispersive spectrometry especially in a scanning electron microscope.

In this sense, the method for studying the zone Z1 will seek to determine the mass-thickness of the object 2 at the level of the zone studied Z1 and then to determine the concentration of each chemical element identified. Accordingly, the method for studying the zone Z1 of the object 2 comprises a step E3 of measuring, for each chemical element identified, a corresponding intensity of an X-ray radiation $I_{iec}$ emergent from the object 2 on account of the said exposure step, a step E4 of determining a value of the said mass-thickness dependent on each measurement step, and a step E5 of determining a value of the concentration of each chemical element identified using the said value of the mass-thickness determined.

The measurement of each intensity of the emergent X-ray radiation $I_{iec}$ is in particular carried out by energy dispersive or wavelength dispersive spectrometry.

The expression "value of the mass-thickness determined" is understood to mean a value of the real mass-thickness of the object that is obtained in particular by calculation.

It is therefore understood that the method for studying the zone Z1 of the object 2 makes it possible to take into account the mass-thickness within the framework of the determination of the concentration of each chemical element.

The scheme implemented in the present method of study making it possible to determine the value of the mass-thickness and the value of the concentration of each chemical element identified advantageously uses a principle of iterative approximation. In this sense, we shall choose, either in an arbitrary manner, or on the basis of assumptions, an intermediate value of mass-thickness and an intermediate value of concentration of each chemical element. Thereafter, these intermediate values are modified in an iterative manner by injections into suitable functions so as to obtain modified corresponding intermediate values.

When the variation of the intermediate values between two successive iterations is less than a predetermined threshold, for example less than a variation of 0.1%, then it is considered that the real values of mass-thickness of the object and of concentration of the corresponding chemical elements are attained.

In a more detailed manner, the method of study can comprise an initialization step E6 (FIG. 3) in which an intermediate value of the mass-thickness $\rho z_0$, with $\rho$ the assumed density and $z_0$ the assumed thickness of the object 2 at the level of the said zone Z1, and an intermediate value of concentration $C_{ic}$ of each chemical element identified are determined by choice. This step E6 is generally carried out between step E3 and step E4.

Preferably, the said choice for each chemical element identified of the intermediate value of concentration $C_{ic}$ is made by considering that the intensity of the corresponding emergent X-ray radiation $I_{iec}$ is equal to the intensity of the radiation $I_{igc}$ generated in the object 2 by the said corresponding chemical element. The intermediate value of the mass-thickness $\rho z_0$ can then also be determined as a function of this consideration.

More particularly, to calculate a mass-thickness $\rho z_0$ subsequent use will be made of an incidence correction general term $\overline{\Theta}$ and for each chemical element identified an incidence correction term $\overline{\Theta}_{im}$ for the said corresponding chemical element, an atomic number correction term $\overline{\varphi}_i$ for the said corresponding chemical element and an absorption correction term $\overline{\chi}_i$ for the said corresponding chemical element.

Thus, with reference to what was stated hereinabove, the choice can suppose as initial condition that the incidence correction general term $\overline{\Theta}$ (calculated for the compound, that is to say the zone of the object), and the atomic number and absorption correction terms $\overline{\varphi}_i$ and $\overline{\chi}_i$ for each constituent i are equal to 1. In this case we have for chosen intermediate value of the mass-thickness $\rho z_0$:

$$\rho z_0 = \cos\theta \Sigma_{i=1}^{N} \xi_i I_{iec} \qquad (\text{eq. 1})$$

With $\xi_i$ the zeta-factor associated with the said corresponding chemical element, and $I_{iec}$ the measured intensity of the emergent X-ray radiation for the said corresponding chemical element.

In the present description, the zeta-factor $\xi_i$ is advantageously that as defined by Watanabe M. and Williams D. B. (2006) in "The quantitative analysis of thin specimens: a review of progress from the Cliff-Lorimer to the new ξ-factor methods, Journal of Microscopy", vol. 221, p. 89-109, 2006. The zeta-factor $\xi_i$ being in particular determined on the basis of a totally transparent wafer ($\overline{\varphi}_i=1$) composed exclusively of the pure corresponding chemical element in the following manner:

$$\xi_i = \lim_{\rho z_0 \to 0} \frac{\rho z_0}{I_{igp}} \qquad (\text{eq. 2})$$

With $I_{igp}$ the intensity of the X-ray radiation generated by the corresponding pure chemical element, for example measured experimentally or simulated by means of a statistical model of Monte-Carlo type.

And we have for chosen intermediate value of concentration $C_{ic}$ of the chemical element i:

$$C_{ic} = \frac{\xi_i}{\rho z_0} I_{iec} \cos\theta \qquad (\text{eq. 3})$$

with $\rho z_0$ obtained on the basis of equation (eq. 1).

After the appropriate choice of the intermediate values of concentration $C_{ic}$ and of the mass-thickness $\rho z_0$ in the course of the initialization step E6, the method of study comprises an iterative cycle of steps E7 comprising, for each iteration of the said cycle E7, a step E7-0 of calculating the incidence correction term $\overline{\Theta}$ intended to take account of the angle of incidence $\theta$ of the electron beam and associated with the zone Z1 studied. The cycle furthermore comprises, for each iteration, a fitting step E7-1, implemented for each chemical element identified. This fitting step E7-1 comprising a step E7-1-1 of calculating an incidence correction term $\overline{\Theta}_{im}$ associated with the said chemical element identified and intended to take account of the angle of incidence $\theta$ of the electron beam 1.

Hereinafter, when one speaks of a term calculated in the course of the said cycle, one is speaking of that calculated in the course of the current iteration of the said cycle.

According to a particular example, the steps of calculating the two incidence correction terms $\overline{\Theta}$ and $\overline{\Theta}_{im}$ comprise respectively the solving of the following equations:

$$\overline{\Theta} = \left\{1 + \left[\frac{\rho z_0}{\cos\theta} f(\mathcal{Z}_c) - 2\frac{\cos\theta}{\rho}\left(1 - e^{14(1-\rho)\frac{\rho z_0}{\cos\theta}f(\mathcal{Z}_c)}\right)e^{-2\frac{\rho z_0}{\cos\theta}f(\mathcal{Z}_c)}\right]\left[\frac{1}{\cos\theta} - 1\right]\right\}^{0.6} \quad (eq.\ 4)$$

for step E7-0

$$\overline{\Theta}_{im} = \left\{1 + \left[\frac{\rho z_{im}}{\cos\theta}f_m(E_{is}) - 2\frac{\cos\theta}{\rho}e^{-2\frac{\rho z_{im}}{\cos\theta}f_m(E_{is})}\right]\left[\frac{1}{\cos\theta} - 1\right]\right\}^{0.6} \quad (eq.\ 5)$$

for each step E7-1-1
with $\mathcal{Z}_c$ the mean atomic number of the object at the level of the said zone, $f(\mathcal{Z}_c)$ a function of the mean atomic number $\mathcal{Z}_c$, $z_{im}$ the maximum ionization depth of the corresponding chemical element, $f_m(E_{is})$ a function of the ionization threshold energy $E_{is}$ of the energy level considered of a corresponding identified chemical element. Of course, it is clear that in equations (eq. 4) and (eq.5) the intermediate value of the mass-thickness $\rho z_0$ is that at the time at which the corresponding step cycle is initiated (whether this be that chosen within the framework of the first iteration or that modified during the successive iterations).

More particularly, $z_{im}$ is determined in a manner known by the person skilled in the art, in particular by applying:

$$z_{im} = \frac{64(E_0^{1.68} - E_{is}^{1.68})}{\rho} \quad (eq.\ 6)$$

With $E_{is}$ the ionization threshold energy of the energy level considered for the said corresponding chemical element (in keV).

According to a particular embodiment, we have:

$$f(\mathcal{Z}_c) = e^{a(Ln\mathcal{Z}_c)^4 + b(Ln\mathcal{Z}_c)^3 + c(Ln\mathcal{Z}_c)^2 + dLn\mathcal{Z}_c + e} \quad (eq.\ 7)$$

with a, b, c, d, e parameters determined by Monte-Carlo simulation and depending on the energy of the electrons of the electron beam. In particular, FIG. 4 illustrates an example of determining the parameters of the function $f(\mathcal{Z}_c)$ by Monte-Carlo simulation for an energy $E_0$ of 30 kV. Thus, knowing $E_0$, it is easy to derive the parameters a, b, c, d which in the example of 30 kV are respectively equal to 0.0314, −0.4661, 2.2686, −3.8452 and −7.6463.

According to a particular embodiment, we have $$f_m(E_{is}) = \frac{AE_{is}^m}{(R_p/S_p)_i} \quad (eq.\ 8)$$

with $(R_p/S_p)_i$ the ratio of the backscattering coefficients $R_p$ and of the stopping power $S_p$ for the corresponding pure chemical element, and A and m parameters determined by Monte-Carlo simulation and depending on the energy level considered for the said corresponding chemical element (the energy level corresponds to the electron shells of the atom excited by the electron beam). And with as seen previously $E_{is}$ the ionization threshold energy of the energy level considered. FIG. 5 gives an example of determining the parameters of the function $f_m(E_{is})$ by Monte-Carlo simulation, the parameters of the function depending on the energy level considered and dependent on the electron shells K, L or M excited by the electron beam.

It should be noted that in the present description, if at the time of a calculation $z_0 \geq z_{im}$, then the thickness $z_0$ is modified in such a way that it is equal to $z_{im}$ before being used in the calculation.

Returning to the fitting step E7-1, the latter comprises a step E7-1-2 of calculating the atomic number correction term $\overline{\varphi}_i$ for the said corresponding chemical element. In particular, this calculation step uses the two incidence correction terms $\overline{\Theta}$ and $\overline{\Theta}_{im}$ described hereinabove calculated in the course of the said cycle, these calculated terms being those belonging to the said step cycle in progress, stated otherwise step E7-1-2 is carried out after step E7-1-1.

According to a particular implementation, each step of calculating the atomic number correction term $\overline{\varphi}_i$ uses the following relation:

$$\overline{\varphi}_i(\rho z_\theta) = \frac{1 + \alpha(\rho z_\theta)^n}{1 + \frac{\alpha C_{ic}}{\xi_i I_{igco}} \frac{(\rho z_\theta)^{(1+n)}}{\left(1 + \frac{\beta_i}{(\rho z_\theta)^n}\right)}} \quad (eq.\ 9)$$

with $I_{igco}$ the intensity per unit time of an X-ray radiation generated by the corresponding chemical element in the object considered to be opaque to the said electron beam 1, $\xi_i$ the zeta-factor associated with the said corresponding chemical element, n a parameter depending on the mean atomic number Zc of the object at the level of the said zone Z1, $\alpha$ a parameter depending on the mean atomic number Zc of the object at the level of the said zone Z1, $\beta_i$ a term making it possible to fit the maximum of the term $\overline{\varphi}_i$ and $z_\theta$ the thickness in the direction of incidence determined on the basis of the incidence correction terms $\overline{\Theta}$ and $\overline{\Theta}_{im}$, calculated in the course of the said cycle (during steps E7-0 and E7-1-1 which are implemented before this step E7-1-2), especially in the manner as indicated hereinabove by using equations (eq. 4) to (eq. 8) hereinabove.

In particular, the parameter n is determined by the following relation:

$$n = n_1 \ln \mathcal{Z}_c + n_2 \quad (eq.\ 10)$$

with the parameters $n_1$ and $n_2$ given by a chart giving the value of n as a function of $\bar{Z}_c$ whatever the power of the electron beam. FIG. 6 specifically shows the variation of the parameter n as a function of the mean atomic number $\bar{Z}_c$ for various known powers of the electron beam. In particular, it has been able to be deduced from this FIG. 6 that $n_1$ was preferentially equal to −0.266 and $n_2$ was preferentially equal to 2.222 in this sense, the application of the Napierian logarithm to the corresponding value of the mean atomic number can be sufficient to solve equation (eq. 10).

It was specified hereinabove that the parameter α was dependent on the mean atomic number $\bar{Z}_c$, in particular the parameter α is determined by the following relation:

$$\alpha = e^{(a_1(Ln\bar{Z}_c)^2 + a_2 Ln\bar{Z}_c + a_3)} \qquad \text{(eq. 11)}$$

with $\alpha_1$, $\alpha_2$ and $\alpha_3$ parameters depending on the initial energy $E_0$ of the electrons of the electron beam. FIG. 7 illustrates the variation of the parameter α as a function of the mean atomic number $\bar{Z}_c$ for various known powers of the electron beam (here 10 kV, 20 kV and 30 kV).

It is understood that the parameters n and α have been defined empirically by fitting the term $\bar{\varphi}_i$ calculated with equation (eq. 9) to the values deduced from the simulations for the set of pure chemical elements and objects studied. For example, the simulation of the atomic number correction term $\bar{\varphi}_i$ for various compositions and thicknesses of wafer at 30 kV is illustrated in FIG. 8. In this FIG. 8, the data points are calculated using the intensities of the X-ray radiation generated by Monte-Carlo simulation and the dashed curves are calculated and fitted to the data points by optimizing the parameters n and α.

The term $\beta_i$ is determined by supposing that, for any thickness greater than or equal to a maximum ionization depth $z_{im}$ of the corresponding chemical element, the intensity of the X-ray radiation generated in the object 2 is equivalent to that of the object 2 if the latter is opaque to the said electron beam. The term $\beta_i$ is then given by the following equation:

$$\beta_i = \begin{cases} (\rho z_{im})^n \dfrac{\left(\dfrac{\xi_i}{C_{ic}} \dfrac{I_{igco}}{\rho z_{im}} - 1\right)}{\alpha(\rho z_{im})^n - \left(\dfrac{\xi_i}{C_{ic}} \dfrac{I_{igco}}{\rho z_{im}} - 1\right)}, & \text{if } \beta_i > 0 \\ 0, & \text{if } \beta_i \leq 0 \end{cases} \qquad \text{(eq. 12)}$$

The parameters used in the calculation of $\beta_i$ being those defined previously and especially in the course of the said cycle of steps in progress.

The term $\beta_i$, although advantageous, can be neglected ($\beta_i = 0$) when the thickness $z_0$ of the object 2 is at least twice as small as a thickness $\bar{z}_i$ (defined hereinafter) for which the atomic number correction term $\bar{\varphi}_i$ is a maximum.

The thickness $\bar{z}_i$ is then calculated by solving the following equation, especially by iterative calculation:

$$(\rho \bar{z}_i)^{1+n} = \dfrac{n\xi_i I_{igco}(1 + \beta_i/(\rho \bar{z}_i)^n)^2 - \rho \bar{z}_i[1 + n + (1+2n)\beta_i/(\rho \bar{z}_i)^n]}{\alpha[1 + (1+n)\beta_i/(\rho \bar{z}_i)^n]} \qquad \text{(eq. 13)}$$

With n, α and $\beta_i$ defined by relations (eq. 10), (eq. 11) and (eq. 12) respectively.

According to a particular embodiment, the term $\bar{z}_i$ can be calculated through the following equation:

$$\bar{z}_i = \bar{z}_{ip} \dfrac{\rho_i}{\rho} \dfrac{n}{n_i}\left[1 + 0.048\left(2.5 - \dfrac{E_0}{20}\right)\left(1 - LnM_i + \dfrac{(LnM_i)^2}{3}\right)\left(\dfrac{M_c}{M_i} - 1\right)\right] \qquad \text{(eq. 14)}$$

with $\bar{z}_{ip}$ the thickness for which the atomic number correction term $\bar{\varphi}_i$ for the corresponding pure chemical element is a maximum, n and $n_i$ the parameters depending respectively on the mean atomic number of the object and on the atomic number of the corresponding pure element in particular as defined in equation (eq. 10) hereinabove ($n_i$ can be calculated with equation 10 by replacing Zc by Zi of the pure chemical element), ρ and $\rho_i$ the densities respectively of the object and of the corresponding pure chemical element and $M_c$ and $M_i$ the atomic masses of the object and of the corresponding pure chemical element.

Although equation 14 gives an approximate value, it will be preferred to equation 13 which gives the exact result, since it is less greedy in terms of calculational resources.

The thickness $\bar{z}_{ip}$ of the corresponding pure chemical element is calculated by solving equation 13. This can be done upstream just once for each chemical element so that the method uses a reading of $\bar{z}_{ip}$ in a table whose input is the chemical element identified.

Concerning the thickness $z_\theta$ which corresponds to the thickness traversed by the electron beam in the direction of incidence θ, it can be deduced on the basis of the two incidence correction terms $\bar{\Theta}$ and $\bar{\Theta}_{im}$, by supposing in particular the following equations:

$$z_\theta = \text{Min}\left(\dfrac{z_0}{\bar{\Theta}\cos\theta}, z_{i\theta}\right) \qquad \text{(eq. 15)}$$

$$z_{i\theta} = \dfrac{z_{im}}{\bar{\Theta}_{im}\cos\theta} \qquad \text{(eq. 16)}$$

With $z_\theta$ the thickness in the direction of incidence θ taking into account the angle of incidence θ and $z_{i\theta}$ the maximum thickness of ionization of the corresponding chemical element according to the direction of incidence θ.

Furthermore, the fitting step E7-1 comprises a step E7-1-3 of calculating an absorption correction term $\bar{\chi}_i$ for the said corresponding chemical element. The purpose of this absorption correction term $\bar{\chi}_i$ is to take into account the absorption by the object of the X-ray radiation generated by the corresponding chemical element. Stated otherwise, the absorption correction term $\bar{\chi}_i$ makes it possible to correct the influence of the object on the X-ray radiation generated. In particular, the calculation of the absorption correction term $\bar{\chi}_i$ for the said corresponding chemical element uses the incidence correction terms $\bar{\Theta}$ and $\bar{\Theta}_{im}$ calculated in the course of the said cycle, as well as the atomic number correction term $\bar{\varphi}_i$, calculated in the course of the said cycle (it is understood that step E7-1-3 is then implemented after step E7-1-1, step E7-1-2 and step E7-0).

According to a particular embodiment, each step of calculating the absorption correction term $\bar{\chi}_i$ makes use of solving the equation $$\bar{\chi}_i = \qquad \text{(eq. 17)}$$

$$\begin{cases} \dfrac{\chi_{ic}\rho z_0 \bar{\varphi}_i(\rho z_\theta)}{\varphi_i(0) + \dfrac{P_i}{\chi_{ic}} +} , & \text{if } z_{ib} > 0 \\[2ex] \dfrac{\left\{P_i'\left(\dfrac{1}{\chi_{ic}} - \rho z_0\right) - \left[\varphi_i(0) - \varphi_i(\rho z_0) + \dfrac{P_i}{\chi_{ic}}\right] + \right\}}{(P_i' - P_i)\rho z_{ib}} \\[2ex] \dfrac{e^{-\chi_{ic}\rho z_{ib}} - \left[\varphi_i(\rho z_0) + \dfrac{P_i'}{\chi_{ic}}\right]e^{-\chi_{ic}\rho z_0}}{\rho z_0 \chi_{ic}\bar{\varphi}_i(\rho z_\theta)} \\[2ex] \dfrac{\rho z_0 \chi_{ic}\bar{\varphi}_i(\rho z_\theta)}{\varphi_i(0) + \dfrac{P_i''}{\chi_{ic}} - \left\{P_i''\left(\dfrac{1}{\chi_{ic}} + \rho z_0\right) + \varphi_i(0)\right\}e^{-\chi_{ic}\rho z_0}} , & \text{if } z_{ib} \leq 0 \end{cases}$$

With $\bar{\varphi}_i(0)$ the value of the distribution $\bar{\varphi}_i(\rho z)$ of the intensities of the X-ray radiation generated at the surface of the object by the corresponding chemical element, with z in $\bar{\varphi}_i(\rho z)$ varying from 0 to $z_0$, $\bar{\varphi}_i(\rho z_0)$ the value of the distribution $\bar{\varphi}_i(\rho z)$ of the intensities of the X-ray radiation generated at the depth $z_0$ of the object by the corresponding chemical element (also called the term for the ionization at the depth $z_0$), $P_i$ the initial slope of the distribution $\bar{\varphi}_i(\rho z)$ of the intensities of the X-ray radiation generated at the surface of the object by the corresponding chemical element and determined in the following manner:

$$P_i = \frac{g \cdot h^4 \cdot (F/\bar{R})^2}{\bar{\varphi}_i(\rho z_{i\theta})\rho z_{i\theta}} \frac{1}{(\cos\theta)^4} \qquad \text{(eq 18)}$$

With $\bar{\varphi}_i(\rho z_{i\theta})$ calculated with eq. 9 by replacing $z_\theta$ with $z_{i\theta}$, $z_{i\theta}$ determined by equation 16 and g, h and (F/$\bar{R}$) parameters known to the person skilled in the art, in particular determined according to the publication of Pouchou J. L. and Pichoir F. (1991) on page 40 "Quantitative analysis of homogeneous or stratified microvolumes applying the model PAP, Electron Probe Quantitation, In: Heinrich & Newbury (Eds) Plenum Press, New York, p. 31"

In particular, employing the terms of the present description, we have:

$$g = 0.22\left(1 - 2e^{-\frac{\bar{Z}_C}{15}\left(\frac{E_0}{E_{is}}-1\right)}\right)\ln(4\bar{Z}_C) \qquad \text{(eq. 18a)}$$

$$h = 1 - 10\frac{1 - \dfrac{1}{1 + \dfrac{E_0}{10E_{is}}}}{\bar{Z}_C^2} \qquad \text{(eq. 18b)}$$

$$F/\bar{R} = 1 + \frac{[1 + 1.3\ln(\bar{Z}_C)]\ln\left[1 + \left(0.2 + \dfrac{\bar{Z}_C}{200}\right)\left(1 - \left\{\dfrac{E_{is}}{E_0}\right\}^{0.42}\right)\right]}{\ln\left(1 + 0.2 + \dfrac{\bar{Z}_C}{200}\right)} \qquad \text{(eq. 18c)}$$

$\chi_{ic}$ is the mass absorption coefficient of the compound for the characteristic X-ray radiation of the corresponding chemical element:

$$\chi_{ic} = \text{cosec}(\psi+\theta)\Sigma_{i+1}^N C_{ic}(\mu/\rho)_i^{ip} \qquad \text{(eq 19)}$$

With the angle of elevation of the X-ray detector with respect to the normal, $\theta$ the angle of incidence of the electron beam, $C_{ic}$ the concentration of the chemical element and $(\mu/\rho)_i^{ip}$ the mass absorption coefficient of the pure chemical element.

Furthermore, $\bar{\varphi}_i(\rho z_\theta)$ is the atomic number correction term defined by eq.9 and calculated in the course of the said cycle.

Still within the framework of equation 17, we have:

$$P_i' = \frac{[\varphi_i(0) - \varphi_i(\rho z_0)]^2 + 2P_i\rho z_0[\bar{\varphi}_i(\rho z_\theta) - \varphi_i(\rho z_0)]}{\rho z_0[2\bar{\varphi}_i(\rho z_\theta) - 2\varphi_i(0) - P_i\rho z_0]}, \qquad \text{(eq. 20)}$$

$$P_i'' = 2\frac{\bar{\varphi}_i(\rho z_\theta) - \varphi_i(0)}{\rho z_0}, \qquad \text{(eq. 21)}$$

and $$z_{ib} = z_0 \frac{2\bar{\varphi}_i(\rho z_\theta) - \varphi_i(0) - \varphi_i(\rho z_0)}{P_i\rho z_0 + \varphi_i(0) - \varphi_i(\rho z_0)}. \qquad \text{(eq. 22)}$$

In particular, $z_\theta$ is obtained according to equations 15 and 16 which depend on the incidence correction terms calculated in the course of the said cycle.

Within the framework of equation eq. 17 making it possible to calculate the absorption correction term $\bar{\chi}_i$, the parameter $\varphi_i(0)$ can be calculated in the following manner:

$$\varphi_i(0) = \begin{cases} 1 + [\varphi_{im}(0) - 1]\dfrac{z_0}{\bar{z}_i}, & \text{if } z_0 < \bar{z}_i \\ \varphi_{im}(0), & \text{if } z_0 \geq \bar{z}_i \end{cases} \qquad \text{(eq. 23)}$$

with $\bar{z}_i$ as defined by equations eq. 13 or 14 and $\varphi_{im}(0)$ the surface ionization of the corresponding chemical element in the object considered to be opaque to the said electron beam and determined in a manner known to the person skilled in the art, in particular determined according to the publication of Pouchou J. L. and Pichoir F. (1991) Quantitative analysis of homogeneous or stratified microvolumes applying the model PAP, Electron Probe Quantitation, In: Heinrich & Newbury (Eds) Plenum Press, New York, p. 31 in the guise of surface ionization term.

According to a particular implementation of the step of calculating the absorption correction term making it possible to optimize the calculated value, the calculation step comprises a step of determining a parameter $\bar{z}_{i\theta}$ corresponding to the minimum value between $\bar{z}_i$ defined by equations eq. 13 or eq. 14 and $z_{i\theta}$ defined by equation eq. 16 and defined by the relation:

$$\bar{z}_{i\theta} = \text{Min}(\bar{z}_i, z_{i\theta}) \qquad \text{(eq 24)}$$

The term $\bar{\varphi}_i(\rho z_0)$ is determined in the following manner:

$$\varphi_i(\rho z_0) = \qquad \text{(eq. 25)}$$

$$\begin{cases} \left\{\left[\dfrac{3}{2} - \varphi_i(0)\right]\dfrac{z_0}{\bar{z}_{i\theta}}\left[2 - \dfrac{z_0}{\bar{z}_{i\theta}}\right] + \varphi_i(0)\right\}\cos\theta, & \text{if } z_0 < \bar{z}_{i\theta} \\[2ex] \dfrac{3}{2}\left\{\left[\dfrac{z_0 - \bar{z}_{i\theta}}{z_{im} - \bar{z}_{i\theta}}\right]\left[\dfrac{z_0 - \bar{z}_{i\theta}}{z_{im} - \bar{z}_{i\theta}} - 2\right] + 1\right\}\cos\theta, & \text{if } \bar{z}_{i\theta} \leq z_0 \leq z_{im} \\[2ex] 0 & \text{if } z_0 > z_{im} \end{cases}$$

with $\bar{\varphi}_i(0)$ calculated according to equation (eq. 23).

According to an alternative, it is possible to simplify the calculations of the atomic number correction and absorption correction terms in the particular case of a wafer perpendicular to the axis of the beam. In this case, the angle of incidence $\theta$ is zero, the consequence of this being that the two incidence correction terms $\bar{\Theta}$ and $\bar{\Theta}_{im}$ are equal to 1 so that the atomic number correction term $\overline{\varphi}_i$ is determined according to the following equation:

$$\overline{\varphi}_i(\rho z_0) = \frac{1 + \alpha(\rho z_0)^n}{1 + \frac{\alpha C_{ic}}{\xi_i I_{igco}} \frac{(\rho z_0)^{(1+n)}}{\left(1 + \frac{\beta_i}{(\rho z_0)^n}\right)}} \quad \text{(eq. 26)}$$

The parameters of $\overline{\varphi}_i(\rho z_0)$ within the framework of this alternative are such as already described. Still within the framework of this alternative, the absorption correction term can be calculated by solving equation (eq. 17) with the use of equations (eq. 20), (eq. 21), (eq. 22), by replacing in these equations $\overline{\varphi}_i(\rho z_\theta)$ by $\overline{\varphi}_i(\rho z_0)$, with $P_i$ the initial slope of the distribution $\overline{\varphi}_i(\rho z)$—z varying here from 0 to $z_0$—of the intensities of the X-ray radiation generated at the surface of the object by the corresponding chemical element and determined in the following manner:

$$P_i = \frac{g \cdot h^4 \cdot (F/\overline{R})^2}{\overline{\varphi}_i(\rho z_{im})\rho z_{im}} \quad \text{(eq 27)}$$

With $\overline{\varphi}_i(\rho z_{im})$ calculated with eq 26 by replacing $z_0$ with $z_{im}$, $z_{im}$ determined by equation 6 and g, h and (F/$\overline{R}$) known parameters, in particular determined according to the publication of Pouchou J. L. and Pichoir F. (1991) Quantitative analysis of homogeneous or stratified microvolumes applying the model PAP, Electron Probe Quantitation, In: Heinrich & Newbury (Eds) Plenum Press, New York, p. 31

$\chi_{ic}$ the mass absorption coefficient of the characteristic X-ray radiation of the corresponding chemical element:

$$\chi_{ic} = \text{cosec}(\psi) \Sigma_{i=1}^{N} C_{ic}(\mu/\rho)_i^{ip} \quad \text{eq 28}$$

Within the framework of the zero angle of incidence; the term $\overline{\varphi}_i(\rho z_0)$ is determined in the following manner:

$$\varphi_i(\rho z_0) = \begin{cases} \left[\frac{3}{2} - \varphi_i(0)\right]\frac{z_0}{\overline{z}_i}\left[2 - \frac{z_0}{\overline{z}_i}\right] + \varphi_i(0), & \text{if } z_0 < \overline{z}_i \\ \frac{3}{2}\left\{\left[\frac{z_0 - \overline{z}_i}{z_{im} - \overline{z}_i}\right]\left[\frac{z_0 - \overline{z}_i}{z_{im} - \overline{z}_i} - 2\right] + 1\right\}, & \text{if } \overline{z}_i \leq z_0 \leq z_{im} \\ 0 & \text{if } z_0 > z_{im} \end{cases} \quad \text{(eq. 29)}$$

$\varphi_i(0)$ defined by eq.23, $\overline{z}_i$ defined according to equations 13 or 14.

Various ways of calculating the atomic number correction and absorption correction terms were seen previously.

Once these terms have been calculated, the said cycle of steps E7 comprises a step E7-2 of modifying the intermediate value of mass-thickness $\rho z_0$ using the incidence correction term $\overline{\Theta}$ calculated in the course of the said cycle, and the incidence correction $\overline{\Theta}_{im}$, atomic number correction $\overline{\varphi}_i$ and absorption correction $\overline{\chi}_i$ terms calculated in the course of the said cycle for each chemical element and dependent on each measurement step E3.

In particular, the intermediate value of mass-thickness can be determined according to the following formulation:

$$\rho z_0 = \overline{\Theta} \cos\theta \sum_{i=1}^{N} \xi_i \frac{I_{igc}}{\overline{\varphi}_i} \quad \text{(eq. 30)}$$

With the application of the following formulation for the intensity of the X-ray radiation generated by the chemical element i in the object $I_{igc}$:

$$I_{igc} = \overline{\chi}_i I_{iec} \quad \text{(eq. 31)}$$

In these formulae, it is clearly understood that for each cycle E7 it is the values calculated in the course of the said cycle E7 of the incidence correction, atomic number correction and absorption correction terms which are used to modify in the course of the same cycle the intermediate values of mass-thickness and of concentration.

Furthermore, the said cycle of steps E7 comprises a step E7-3 of modifying, for each chemical element, the intermediate value of concentration $C_{ic}$ of the said corresponding chemical element using the intermediate value of mass-thickness $\rho z_0$ as modified in the course of the said cycle, the incidence correction term $\overline{\Theta}$, calculated in the course of the said cycle, and the incidence correction $\overline{\Theta}_{im}$, atomic number correction $\overline{\varphi}_i$ and absorption correction $\overline{\chi}_i$ terms calculated in the course of the said cycle and corresponding to the said chemical element.

Stated otherwise, in the course of each cycle E7 the intermediate value of the mass-thickness is modified (step E7-2) according to the following formula $$\rho z_0 = \overline{\Theta} \cos\theta \sum_{i=1}^{N} \xi_i \frac{\overline{\chi}_i I_{iec}}{\overline{\varphi}_i} \quad \text{(eq. 32)}$$

with N the total number of chemical elements identified, i the index of the current chemical element studied, $I_{iec}$ the intensity of the emergent X-ray radiation corresponding to the said chemical element of index i, $\overline{\chi}_i$ the absorption correction term calculated in the course of the said cycle and corresponding to the said chemical element of index i, $\xi_i$ the zeta-factor associated with the said chemical element of index i, the atomic number correction term $\overline{\varphi}_i$ calculated in the course of the said cycle and corresponding to the said chemical element of index i, $\overline{\Theta}$ the incidence correction term calculated in the course of the said cycle.

In particular, for each chemical element, the intermediate value of concentration $C_{ic}$, can be calculated (step E7-3) using the following formula:

$$C_{ic} = \frac{\xi_i}{\rho z_0} \frac{I_{igc}}{\overline{\varphi}_i} \overline{\Theta} \cos\theta \quad \text{(eq. 33)}$$

In which $I_{igc}$ is determined according to equation (eq. 31), $\rho z_0$ corresponds to the mass-thickness value as modified in the course of the said corresponding cycle of steps, $\Theta$ corresponding to the incidence correction term calculated in the course of the said cycle and $\overline{\varphi}_i$ corresponding to the atomic number correction term as calculated in the course of the said corresponding cycle of steps. Stated otherwise, in the course of each cycle the intermediate value of concentration $C_{ic}$ of each chemical element is calculated according to the following formula:

$$C_{ic} = \frac{\xi_i}{\rho z_0} \frac{\overline{\chi}_i I_{iec}}{\overline{\varphi}_i} \overline{\Theta} \cos\theta \quad \text{(eq. 34)}$$

with $I_{iec}$ the measured intensity of the emergent X-ray radiation of the said corresponding chemical element, $\rho z_0$ the intermediate mass-thickness value modified in the course of the said cycle, $\bar{\chi}_i$ the absorption correction term for the said corresponding chemical element calculated in the course of the said cycle, $\xi_i$ the zeta-factor associated with the said corresponding chemical element, $\bar{\Theta}$ the incidence correction term calculated in the course of the said cycle, the atomic number correction term $\bar{\varphi}_i$ calculated in the course of the said cycle for the said corresponding chemical element.

The iteration of the step E7 cycle is halted when the variation, between two successive iterations of the intermediate values of mass-thickness $\rho z_0$ and of the intermediate values of concentration $C_{ic}$ of each chemical element, is less than an associated predetermined threshold, the said modified intermediate mass-thickness value defining the mass-thickness value determined and each modified intermediate concentration value defining the corresponding concentration value determined.

The method described hereinabove makes it possible to study a precise zone of the object. According to need, it may be useful to analyse the object in its entirety. In this sense, the invention also relates to a method for studying an object comprising the following steps:

Dividing the object into several zones to be studied,
Implementing, for each zone, the said method of study as described previously with a view to determining the corresponding mass-thickness value and, for each chemical element of the said zone, the corresponding concentration value.

The methods described hereinabove make it possible in particular to calculate the thickness and the composition of a semi-transparent/semi-opaque thin wafer on the basis of a measurement by EDS (energy dispersive spectrometry) in an SEM (scanning electron microscope), it not being possible to do this using any current scheme, namely neither the k-factor scheme, nor the $\varphi\rho z$ scheme. Moreover, the invention combines both precision and speed of the calculations making it possible to produce, in real time, reliable profiles and maps, to better than 5% in most cases, of the distribution of the mass-thicknesses and concentrations.

In a general manner, the methods described hereinabove are potentially of interest to all EDS system constructors for SEM in so far as it allows the simultaneous analysis of the composition and the mass-thickness of any homogeneous type of materials, whatever its thickness and its composition. At least two types of materials are concerned:

thin wafers prepared by FIB for "Focused Ion Beam" (thicknesses varying between 100 and 300 nm) or by any other polishing technique (ultra-microtomy, mechanical, chemical or ion polishing), any type of materials deposited on a transparent TEM ("Transmission Electron Microscope") grid (nanowires, nanoparticles, etc.).

Another application relates to the characterization of reference thin wafers for EDS quantitative analysis in transmission electron microscopy (TEM). Indeed, quantitative analysis by TEM/EDS requires calibration of the spectrometer by means of reference thin wafers whose composition and thickness must be determined beforehand.

The invention claimed is:

1. Method for studying a zone of an object, the zone exhibiting a mass-thickness and comprising at least one chemical element, wherein the method comprises:
a step of exposing a part of the zone of the object to an electron beam, wherein the part of the zone of the object is selected irrespective of the mass-thickness of the object in the part of the zone, provided the exposure step is carried out so that the electron beam is partially transmitted by the object in a manner allowing measuring for each chemical element identified, a corresponding intensity of an X-ray radiation emergent from the object on account of the exposure step, a step of identifying each chemical element present in the zone by virtue of the exposure step, a step of measuring, for each chemical element identified, the corresponding intensity of an X-ray radiation emergent from the object on account of the exposure step, a step of determining a value of the mass-thickness dependent on each measurement step, a step of determining a value of the concentration of each chemical element identified using the value of the mass-thickness determined, wherein the method comprises an initialization step in which an intermediate value of the mass-thickness $\rho z_0$, with $\rho$ an assumed density and $z_0$ an assumed thickness of the object at the level of the zone, and an intermediate value of concentration $C_{ic}$ of each chemical element identified are determined by choice, and wherein the method comprises an iterative cycle of steps comprising for each iteration of the said cycle:

a step of calculating an incidence correction term $\bar{\Theta}$ intended to take account of an angle of incidence $\theta$ of the electron beam and associated with the zone studied, a fitting step, implemented for each chemical element identified, and comprising:

a step of calculating an incidence correction term $\bar{\Theta}_{im}$ associated with the chemical element identified and intended to take account of the angle of incidence $\theta$ of the electron beam, a step of calculating an atomic number correction term $\varphi_i$ for the corresponding chemical element using the incidence correction terms $\bar{\Theta}$ and $\bar{\Theta}_{im}$ calculated in the course of the said cycle, a step of calculating an absorption correction term $\bar{\chi}_i$ for the corresponding chemical element using the incidence correction terms $\bar{\Theta}$ and $\bar{\Theta}_{im}$ calculated in the course of the said cycle and the atomic number correction term $\varphi_i$ calculated in the course of the said cycle, a step of modifying the intermediate value of mass-thickness $\rho z_0$ using the incidence correction term $\bar{\Theta}$ calculated in the course of the cycle and the incidence correction $\bar{\Theta}_{im}$, atomic number correction $\bar{\varphi}_i$ and absorption correction $\bar{\chi}_i$ terms calculated in the course of the cycle for each chemical element and dependent on each measurement step, a step of modifying, for each chemical element, the intermediate value of concentration $C_{ic}$ of the corresponding chemical element using the intermediate value of mass-thickness $\rho z_0$ as modified in the course of the cycle, the incidence correction term $\bar{\Theta}$, calculated in the course of the cycle, and the incidence correction $\bar{\Theta}_{im}$, atomic number correction $\bar{\varphi}_i$ and absorption correction $\bar{\chi}_i$ terms calculated in the course of the cycle and corresponding to the chemical element, wherein the iteration is halted when a variation, between two successive iterations of the intermediate values of mass-thickness $\rho z_0$ and of the intermediate values of concentration $C_{ic}$ of each chemical element, is less than an associated predetermined threshold, the modified intermediate mass-thickness value defining the mass-thickness value determined and each modified intermediate concentration value defining the corresponding concentration value determined.

2. Method according to claim 1, wherein each step of calculating the incidence correction term $\overline{\Theta}$ comprises solving the following equation:

$$\overline{\Theta} = \left\{1 + \left[\frac{\rho z_0}{\cos\theta} f(Z_c) - 2\frac{\cos\theta}{\rho}\left(1 - e^{14(1-\rho)\frac{\rho z_0}{\cos\theta}f(Z_c)}\right)e^{-2\frac{\rho z_0}{\cos\theta}f(Z_c)}\right]\left[\frac{1}{\cos\theta} - 1\right]\right\}^{0.6}$$

and wherein each step of calculating the incidence correction term $\overline{\Theta}_{im}$ comprises solving the following equation:

$$\overline{\Theta}_{im} = \left\{1 + \left[\frac{\rho z_{im}}{\cos\theta} f_m(E_{is}) - 2\frac{\cos\theta}{\rho} e^{-2\frac{\rho z_{im}}{\cos\theta}f_m(E_{is})}\right]\left[\frac{1}{\cos\theta} - 1\right]\right\}^{0.6}$$

with $Z_c$ a mean atomic number of the object at the level of the zone, $f(Z_c)$ a function of the mean atomic number $Z_c$, $z_{im}$ a maximum ionization depth of the corresponding chemical element, $f_m(E_{is})$ a function of an ionization threshold energy $E_{is}$ of the energy level considered of a corresponding chemical element.

3. Method according to claim 2, wherein $$f(Z_c) = e^{a(LnZ_c)^4 + b(LnZ_c)^3 + c(LnZ_c)^2 + dLnZ_c + e},$$

with a, b, c, d, e parameters being determined by Monte-Carlo simulation and depending on an energy of electrons of the electron beam.

4. Method according to claim 3, wherein $$f_m(E_{is}) = \frac{AE_{is}^m}{(R_p/S_p)_i},$$

with $(R_p/S_p)_i$ being the ratio of backscattering coefficients $R_p$ and of a stopping power $S_p$ for the corresponding pure chemical element, and A and m being parameters determined by Monte-Carlo simulation and depending on the energy level for the corresponding chemical element.

5. Method according to claim 2, wherein $$f_m(E_{is}) = \frac{AE_{is}^m}{(R_p/S_p)_i},$$

with $(R_p/S_p)_i$ being the ratio of backscattering coefficients $R_p$ and of a stopping power $S_p$ for the corresponding pure chemical element, and A and m being parameters determined by Monte-Carlo simulation and depending on the energy level for the corresponding chemical element.

6. Method according to claim 2, wherein each step of calculating the atomic number correction term $\varphi_i$ uses the following relation $$\overline{\varphi}_i(\rho z_\theta) = \frac{1 + \alpha(\rho z_\theta)^n}{1 + \frac{\alpha C_{ic}}{\xi_i I_{igco}}\frac{(\rho z_\theta)^{(1+n)}}{\left(1 + \frac{\beta_i}{(\rho z_\theta)^n}\right)}},$$

with $I_{igco}$ an intensity per unit time of an X-ray radiation generated by the corresponding chemical element in the object considered to be opaque to the electron beam, $\xi_i$ a zeta-factor associated with the corresponding chemical element, n a parameter depending on the mean atomic number Zc of the object at the level of the zone, $\alpha$ a parameter depending on the mean atomic number Zc of the object at the level of the zone, $\beta_i$ a term making it possible to fit a maximum of the term $\overline{\varphi}_i$ and $z_\theta$ a thickness in the direction of incidence $\theta$ determined on the basis of the incidence correction terms $\overline{\Theta}$ and $\overline{\Theta}_{im}$ calculated in the course of the cycle.

7. Method according to claim 1, wherein each step of calculating the atomic number correction term $\overline{\varphi}_i$ uses the following relation $$\overline{\varphi}_i(\rho z_\theta) = \frac{1 + \alpha(\rho z_\theta)^n}{1 + \frac{\alpha C_{ic}}{\xi_i I_{igco}}\frac{(\rho z_\theta)^{(1+n)}}{\left(1 + \frac{\beta_i}{(\rho z_\theta)^n}\right)}},$$

with $I_{igco}$ an intensity per unit time of an X-ray radiation generated by the corresponding chemical element in the object considered to be opaque to the electron beam, $\xi_i$ a zeta-factor associated with the corresponding chemical element, n a parameter depending on a mean atomic number Zc of the object at the level of the zone, $\alpha$ a parameter depending on the mean atomic number Zc of the object at the level of the zone, $\beta_i$ a term making it possible to fit a maximum of the term $\overline{\varphi}_i$ and $z_0$ a thickness in the direction of incidence $\theta$ determined on the basis of the incidence correction terms $\overline{\Theta}$ and $\overline{\Theta}_{im}$ calculated in the course of the cycle.

8. Method according to claim 7, wherein the parameter n is determined by the following relation $n = n_1 \, Ln \, Z + n_2$, the parameters $n_1$ and $n_2$ being given by a chart giving a value of n as a function of $Z_c$ whatever a power of the electron beam.

9. Method according to claim 7, wherein the parameter $\alpha$ is determined by the following relation $$\alpha = e^{(\alpha_1 (LnZ_c)^2 + \alpha_2 LnZ_c + \alpha_3)},$$

with $\alpha_1$, $\alpha_2$ and $\alpha_3$ parameters depending on an initial energy $E_0$ of electrons of the electron beam.

10. Method according to claim 7, wherein the term $\beta_i$ is determined by supposing that, for any thickness greater than or equal to a maximum ionization depth $z_{im}$ of the corresponding chemical element, the intensity of the X-ray radiation generated in the object is equivalent to that of the object if the object is opaque to the electron beam.

11. Method according to claim 10, wherein the term $\beta_i$ is obtained by solving the following equation:

$$\beta_i = \begin{cases} (\rho z_{im})^n \dfrac{\left(\dfrac{\xi_i\, I_{igco}}{C_{ic}\, \rho z_{im}} - 1\right)}{\alpha(\rho z_{im})^n - \left(\dfrac{\xi_i\, I_{igco}}{C_{ic}\, \rho z_{im}} - 1\right)}, & \text{if } \beta_i > 0 \\ 0, & \text{if } \beta_i \le 0 \end{cases},$$

with $z_{im}$ being a maximum ionization depth of the corresponding chemical element.

12. Method according to claim 1, wherein each step of calculating the absorption correction term $\overline{\chi}_i$ makes use of solving the equation $$\overline{\chi}_i =$$

$$\begin{cases} \dfrac{\chi_{ic}\rho z_0 \overline{\varphi}_i(\rho z_\theta)}{\varphi_i(0) + \dfrac{P_i}{\chi_{ic}} + \left\{ \begin{array}{l} P'_i\!\left(\dfrac{1}{\chi_{ic}} - \rho z_0\right) - \left[\varphi_i(0) - \varphi_i(\rho z_0) + \dfrac{P_i}{\chi_{ic}}\right] + \\ (P'_i - P_i)\rho z_{ib} \end{array} \right\}}, & \text{if } z_{ib} > 0 \\[4pt] \quad e^{-\chi_{ic}\rho z_{ib}} - \left[\varphi_i(\rho z_0) + \dfrac{P'_i}{\chi_{ic}}\right] e^{-\chi_{ic}\rho z_0} & \\[8pt] \dfrac{\rho z_0 \chi_{ic} \overline{\varphi}_i(\rho z_\theta)}{\varphi_i(0) + \dfrac{P''_i}{\chi_{ic}}\left\{P''_i\!\left(\dfrac{1}{\chi_{ic}} + \rho z_0\right) + \varphi_i(0)\right\} e^{-\chi_{ic}\rho z_0}}, & \text{if } z_{ib} \le 0 \end{cases}$$

with $\varphi_i(0)$ being a value of a distribution of intensities of the X-ray radiation generated at a surface of the object by the corresponding chemical element, $\varphi_i(\rho z_0)$ a value of the distribution of the intensities of the X-ray radiation generated at the depth $z_0$ of the object by the corresponding chemical element, $P_i$ an initial slope of the distribution of the intensities of the X-ray radiation generated at the surface of the object by the corresponding chemical element and determined by the relation $$P_i = \dfrac{g \cdot h^4 \cdot (F/\overline{R})^2}{\overline{\varphi}_i(\rho z_{i\theta})\rho z_{i\theta}} \dfrac{1}{(\cos\theta)^4} \text{ with}$$

$$\overline{\varphi}_i(\rho z_{i\theta}) = \dfrac{1 + \alpha(\rho z_{i\theta})^n}{1 + \dfrac{\alpha C_{ic}}{\xi_i I_{igco}}\dfrac{(\rho z_{i\theta})^{(1+n)}}{\left(1 + \dfrac{\beta_i}{(\rho z_{i\theta})^n}\right)}} \text{ and } z_{i\theta} = \dfrac{z_{im}}{\Theta_{im}\cos\theta},$$

$\chi_{ic}$ representing a mass absorption coefficient of a compound for the characteristic X-ray radiation of the corresponding chemical element, $\overline{\varphi}_i(\rho z_\theta)$ being the atomic number correction term calculated in the course of the cycle, $$P'_i = \dfrac{[\varphi_i(0) - \varphi_i(\rho z_0)]^2 + 2P_i\rho z_0[\overline{\varphi}_i(\rho z_\theta) - \varphi_i(\rho z_0)]}{\rho z_0[2\overline{\varphi}_i(\rho z_\theta) - 2\varphi_i(0) - P_i\rho z_0]},$$

$$P''_i = 2\dfrac{\overline{\varphi}_i(\rho z_\theta) - \varphi_i(0)}{\rho z_0},$$

$$z_{ib} = z_0 \dfrac{2\overline{\varphi}_i(\rho z_\theta) - \varphi_i(0) - \varphi_i(\rho z_0)}{P_i\rho z_0 + \varphi_i(0) - \varphi_i(\rho z_0)},$$

$z_{im}$ a maximum ionization depth of the corresponding chemical element, $\beta_i$ a term making it possible to fit a maximum of the atomic number correction term, $I_{igco}$ an intensity per unit time of an X-ray radiation generated by the corresponding chemical element in the object considered to be opaque to the electron beam, $\xi_i$ a zeta-factor associated with the corresponding chemical element, $\alpha$ a parameter depending on the mean atomic number Zc of the object at the level of the said zone (Z1), n a parameter depending on the mean atomic number Zc of the object at the level of the zone and $z_\theta$ a depth of the object at the level of the zone while taking account of the incidence $\theta$ of the electron beam.

13. Method according to claim 12, wherein the parameter $\varphi_i(0)$ is calculated in the following manner:

$$\varphi_i(0) = \begin{cases} 1 + [\varphi_{im}(0) - 1]\dfrac{z_0}{\overline{z}_i}, & \text{if } z_0 < \overline{z}_i \\ \varphi_{im}(0), & \text{if } z_0 \ge \overline{z}_i \end{cases} \text{ with}$$

$$\overline{z}_i = \overline{z}_{ip}\dfrac{\rho_i}{\rho}\dfrac{n}{n_i}\left[1 + 0.048\!\left(2.5 - \dfrac{E_0}{20}\right)\!\left(1 - LnM_i + \dfrac{(LnM_i)^2}{3}\right)\!\left(\dfrac{M_c}{M_i} - 1\right)\right],$$

$\varphi_{im}(0)$ being a surface ionization of the corresponding chemical element in the object considered to be opaque to the said electron beam, $\overline{z}_{ip}$ a thickness for which the atomic number correction term $\overline{\varphi}_i$ for the corresponding pure chemical element is a maximum, n and $n_i$ parameters depending respectively on the mean atomic number of the object and on the atomic number of the pure chemical element, $\rho_i$ a density of the corresponding pure chemical element and $M_c$ and $M_i$ atomic masses of the object and of the corresponding pure chemical element, and $E_0$ an initial energy of electrons of the electron beam.

14. Method according to claim 13, comprising a step of determining a parameter $\overline{z}_{i\theta}$ corresponding to the minimum value between $\overline{z}_i$ and $z_{i\theta}$ and defined by the following relation: $\overline{z}_{i\theta} = \text{Min}(\overline{z}_i, z_{i\theta})$.

15. Method according to claim 14, wherein the term $\varphi_i(\rho z_0)$ is determined in the following manner:

$$\varphi_i(\rho z_0) = \begin{cases} \left\{\left[\dfrac{3}{2} - \varphi_i(0)\right]\dfrac{z_0}{\overline{z}_{i\theta}}\left[2 - \dfrac{z_0}{\overline{z}_{i\theta}}\right] + \varphi_i(0)\right\}\cos\theta, & \text{if } z_0 < \overline{z}_{i\theta} \\ \dfrac{3}{2}\left\{\left[\dfrac{z_0 - \overline{z}_{i\theta}}{z_{im} - \overline{z}_{i\theta}}\right]\!\left[\dfrac{z_0 - \overline{z}_{i\theta}}{z_{im} - \overline{z}_{i\theta}} - 2\right] + 1\right\}\cos\theta, & \text{if } \overline{z}_{i\theta} \le z_0 \le z_{im} \\ 0 & \text{if } z_0 > z_{im} \end{cases}.$$

16. Method according to claim 1, wherein the angle of incidence $\theta$ being zero then the two incidence correction terms $\overline{\Theta}$ and $\overline{\Theta}_{im}$ are equal to 1 so that the atomic number correction term is determined on the basis of the following equation $$\overline{\varphi}_i(\rho z_0) = \dfrac{1 + \alpha(\rho z_0)^n}{1 + \dfrac{\alpha C_{ic}}{\xi_i I_{igco}}\dfrac{(\rho z_0)^{(1+n)}}{\left(1 + \dfrac{\beta_i}{(\rho z_0)^n}\right)}},$$

with $I_{igco}$ being an intensity per unit time of an X-ray radiation generated by the corresponding chemical element in the object considered to be opaque to the said electron beam, $\xi_i$ a zeta-factor associated with the corresponding chemical element, n a parameter depending on the mean atomic number Zc of the object at the level of the zone, α a parameter depending on the mean atomic number Zc of the object at the level of the zone, $\beta_i$ a term making it possible to fit the maximum of the term $\overline{\varphi}_i$, and wherein $$\overline{\chi}_i = \begin{cases} \dfrac{\chi_{ic}\rho z_0 \overline{\varphi}_i(\rho z_0)}{\varphi_i(0) + \dfrac{P_i}{\chi_{ic}} + \left\{P'_i\left(\dfrac{1}{\chi_{ic}} - \rho z_0\right) - \right.} \\ \left[\varphi_i(0) - \varphi_i(\rho z_0) + \dfrac{P_i}{\chi_{ic}}\right] + (P'_i - P_i)\rho z_{ib}\right\} \\ e^{-\chi_{ic}\rho z_{ib}} - \left[\varphi_i(\rho z_0) + \dfrac{P'_i}{\chi_{ic}}\right]e^{-\chi_{ic}\rho z_0} \end{cases}, \quad \text{if } z_{ib} > 0$$

$$\dfrac{\rho z_0 \chi_{ic}\overline{\varphi}_i(\rho z_0)}{\varphi_i(0) + \dfrac{P''_i}{\chi_{ic}}\left\{P''_i\left(\dfrac{1}{\chi_{ic}} + \rho z_0\right) + \varphi_i(0)\right\}e^{-\chi_{ic}\rho z_0}}, \quad \text{if } z_{ib} \le 0$$

with $$\varphi_i(\rho z_0) = \begin{cases} \left[\dfrac{3}{2} - \varphi_i(0)\right]\dfrac{z_0}{\overline{z}_i}\left[2 - \dfrac{z_0}{\overline{z}_i}\right] + \varphi_i(0), & \text{if } z_0 < \overline{z}_{i\theta} \\ \dfrac{3}{2}\left\{\left[\dfrac{z_0 - \overline{z}_i}{z_{im} - \overline{z}_i}\right]\left[\dfrac{z_0 - \overline{z}_i}{z_{im} - \overline{z}_i} - 2\right] + 1\right\}, & \text{if } \overline{z}_i \le z_0 \le z_{im} \\ 0 & \text{if } z_0 > z_{im} \end{cases},$$

$\varphi_i(0)$ being a value of a distribution of intensities of the X-ray radiation generated at the surface of the object by the corresponding chemical element, $P_i$ an initial slope of the distribution of the intensities of the X-ray radiation generated at the surface of the object by the corresponding chemical element and determined by the relation $$P_i = \dfrac{g \cdot h^4 \cdot (F/\overline{R})^2}{\overline{\varphi}_i(\rho z_{im})\rho z_{im}},$$

with $$\overline{\varphi}_i(\rho z_{im}) = \dfrac{1 + \alpha(\rho z_{im})^n}{1 + \dfrac{\alpha C_{ic}}{\xi_i I_{igco}}\dfrac{(\rho z_{im})^{(1+n)}}{\left(1 + \dfrac{\beta_i}{(\rho z_{im})^n}\right)}},$$

$\chi_{ic}$ representing the mass absorption coefficient of the object for the corresponding chemical element $$P'_i = \dfrac{[\varphi_i(0) - \varphi_i(\rho z_0)]^2 + 2P_i\rho z_0[\overline{\varphi}_i(\rho z_0) - \varphi_i(\rho z_0)]}{\rho z_0[2\overline{\varphi}_i(\rho z_0) - 2\varphi_i(0) - P_i\rho z_0]},$$

$$P''_i = 2\dfrac{\overline{\varphi}_i(\rho z_0) - \varphi_i(0)}{\rho z_0}, \text{ and}$$

$$z_{ib} = z_0 \dfrac{2\overline{\varphi}_i(\rho z_0) - \varphi_i(0) - \varphi_i(\rho z_0)}{P_i \rho z_0 + \varphi_i(0) - \varphi_i(\rho z_0)},$$

$z_{im}$ a maximum ionization depth of the corresponding chemical element, $$\overline{z}_i = \overline{z}_{ip}\dfrac{\rho_i}{\rho}\dfrac{n}{n_i}\left[1 + 0.048\left(2.5 - \dfrac{E_0}{20}\right)\left(1 - LnM_i + \dfrac{(LnM_i)^2}{3}\right)\left(\dfrac{M_c}{M_i} - 1\right)\right],$$

$\overline{z}_{ip}$ a thickness for which the atomic number correction term $\overline{\varphi}_i$ for the corresponding pure chemical element is a maximum, n and $n_i$ parameters depending respectively on the mean atomic number of the object and on the atomic number of the corresponding pure element, $\rho_i$ a density of the corresponding pure chemical element and $M_c$ and $M_i$ atomic masses of the object and of the corresponding pure chemical element, $E_0$ an initial energy of electrons of the electron beam, $\beta_i$ a term making it possible to fit a maximum of the atomic number correction term, $I_{igco}$ an intensity per unit time of an X-ray radiation generated by the corresponding chemical element in the object considered to be opaque to the electron beam, $\xi_i$ a zeta-factor associated with the corresponding chemical element, α a parameter depending on the mean atomic number Zc of the object at the level of the zone, n a parameter depending on the mean atomic number Zc of the object at the level of the zone.

17. Method according to claim 1, wherein in the course of each cycle the intermediate value of the mass-thickness is modified according to the following formula $$\rho z_0 = \overline{\Theta}\cos\theta \Sigma_{i=1}^{N} \xi_i \dfrac{\overline{\chi}_i I_{iec}}{\overline{\varphi}_i},$$

with N being a total number of chemical elements identified, i an index of the current chemical element studied, $I_{iec}$ an intensity of the emergent X-ray radiation corresponding to the chemical element of index i, $\overline{\chi}_i$ an absorption correction term calculated in the course of the cycle and corresponding to the chemical element of index i, $\xi_i$ a zeta-factor associated with the chemical element of index i, the atomic number correction term $\overline{\varphi}_i$ being calculated in the course of the cycle and corresponding to the chemical element of index i, $\overline{\Theta}$ being an incidence correction term calculated in the course of the cycle.

18. Method according to claim 1, wherein in the course of each cycle an intermediate value of concentration $C_{ic}$ of each chemical element is calculated according to the following formula:

$$C_{ic} = \dfrac{\xi_i}{\rho z_0}\dfrac{\overline{\chi}_i I_{iec}}{\overline{\varphi}_i}\overline{\Theta}\cos\theta,$$

with $I_{iec}$ being a measured intensity of the emergent X-ray radiation of the corresponding chemical element, $\rho z_0$ an intermediate mass-thickness value modified in the course of the cycle, $\overline{\chi}_i$ an absorption correction term for the corresponding chemical element calculated in the course of the cycle, $\xi_i$ a zeta-factor associated with the corresponding chemical element, the atomic number correction term $\overline{\varphi}_i$ being calculated in the course of the cycle for the corresponding chemical element, $\overline{\Theta}$ an incidence correction term calculated in the course of the cycle.

19. Method for studying an object comprising:
dividing the object into several zones to be studied,
implementing, for each zone, the method according to claim 1 with a view to determining the corresponding mass-thickness value and, for each element of the said zone, the corresponding concentration value.

20. Method according to claim 1, wherein in the initialization step the intermediate value of the mass-thickness $\rho z_0$ and the intermediate value of concentration $C_{ic}$ of each chemical element identified is determined by considering that the intensity of the corresponding emergent X-ray radiation is equal to an intensity of the radiation generated in the object by the said corresponding chemical element.

21. Method according to claim 1, wherein the method produces a profile of the element composition including mass-thickness and concentration values, wherein the values are provided with an approximation rate lower than 5%.

* * * * *

UNITED STATES PATENT AND TRADEMARK OFFICE
CERTIFICATE OF CORRECTION

PATENT NO. : 10,240,918 B2
APPLICATION NO. : 14/966932
DATED : March 26, 2019
INVENTOR(S) : Eric Robin Page 1 of 1

It is certified that error appears in the above-identified patent and that said Letters Patent is hereby corrected as shown below:

In the Claims

Column 22, Line 46, change:
is determined by the following relation n=$n_1$ Ln Z +$n_2$, the To be:
is determined by the following relation $n = n_1 LnZ_c + n_2$, the Column 26, Line 36, change:
index $\xi_i$ a zeta-factor associated with the chemical To be:
index i, $\xi_i$ a zeta-factor associated with the chemical Signed and Sealed this
Twenty-sixth Day of May, 2020

Andrei Iancu
*Director of the United States Patent and Trademark Office*